(12) United States Patent
Shimokawa et al.

(10) Patent No.: US 11,890,492 B2
(45) Date of Patent: Feb. 6, 2024

(54) DEVICE FOR TREATING DEMENTIA, METHOD FOR OPERATING SAID DEVICE, AND PROGRAM

(71) Applicant: SOUND WAVE INNOVATION CO., LTD., Tokyo (JP)

(72) Inventors: Hiroaki Shimokawa, Miyagi (JP); Hiroshi Kanai, Miyagi (JP); Hirofumi Taki, Miyagi (JP); Kumiko Eguchi, Miyagi (JP); Tomohiro Shindo, Miyagi (JP)

(73) Assignee: SOUND WAVE INNOVATION CO., LTD., Tokyo (JP)

( * ) Notice: Subject to any disclaimer, the term of this patent is extended or adjusted under 35 U.S.C. 154(b) by 172 days.

(21) Appl. No.: 16/498,428

(22) PCT Filed: Mar. 30, 2018

(86) PCT No.: PCT/JP2018/013893
§ 371 (c)(1),
(2) Date: Sep. 27, 2019

(87) PCT Pub. No.: WO2018/181991
PCT Pub. Date: Oct. 4, 2018

(65) Prior Publication Data
US 2020/0289855 A1    Sep. 17, 2020

(30) Foreign Application Priority Data
Mar. 30, 2017   (JP) ................................ 2017-067572

(51) Int. Cl.
*A61N 7/00*    (2006.01)

(52) U.S. Cl.
CPC ........ *A61N 7/00* (2013.01); *A61N 2007/0026* (2013.01); *A61N 2007/0078* (2013.01)

(58) Field of Classification Search
CPC .............. A61N 7/00; A61N 2007/0026; A61N 2007/0078
See application file for complete search history.

(56) References Cited

U.S. PATENT DOCUMENTS

2006/0185083 A1* 8/2006 Sackner ................. A61H 1/006
5/651
2008/0275372 A1   11/2008 Shimotori
(Continued)

FOREIGN PATENT DOCUMENTS

| JP | 200424668 A | 1/2004 |
|----|-------------|--------|
| JP | 2013-503681 A | 2/2013 |

(Continued)

OTHER PUBLICATIONS

Kenichiro Hanawa et al., "Low-Intensity Pulsed Ultrasound Induces Angiogenesis and Ameliorates Left Ventricular Dysfunction in a Porcine Model of Chronic Myocardial Ischemia", PLOS ONE, p. 1-11pp, Aug. 2014, vol. 9, Issue 8, e104863, 11pp.
(Continued)

*Primary Examiner* — Hien N Nguyen
(74) *Attorney, Agent, or Firm* — HAUPTMAN HAM, LLP

(57) ABSTRACT

The present invention provides a device for treating dementia, including: a plurality of ultrasound probes; an ultrasound transducer arranged in each of the ultrasound probes and configured to propagate unfocused ultrasound energy to a brain; and an ultrasound generator connected to each of the ultrasound probes.

13 Claims, 18 Drawing Sheets

(56) References Cited

U.S. PATENT DOCUMENTS

| | | | |
|---|---|---|---|
| 2011/0178441 A1* | 7/2011 | Tyler | A61N 5/0622 |
| | | | 601/2 |
| 2012/0083717 A1 | 4/2012 | Alleman et al. | |
| 2012/0083718 A1 | 4/2012 | Alleman et al. | |
| 2012/0172723 A1* | 7/2012 | Gertner | A61B 8/06 |
| | | | 600/439 |
| 2012/0289869 A1* | 11/2012 | Tyler | A61B 5/245 |
| | | | 601/2 |
| 2013/0012755 A1* | 1/2013 | Slayton | A61N 7/02 |
| | | | 601/3 |
| 2014/0127329 A1* | 5/2014 | Giordano | A61K 45/06 |
| | | | 424/718 |
| 2015/0073400 A1* | 3/2015 | Sverdlik | A61N 7/022 |
| | | | 606/28 |
| 2015/0151142 A1* | 6/2015 | Tyler | A61B 5/055 |
| | | | 601/2 |
| 2016/0001096 A1* | 1/2016 | Mishelevich | A61N 7/02 |
| | | | 601/2 |
| 2016/0243381 A1* | 8/2016 | Alford | A61N 7/00 |
| 2017/0080256 A1* | 3/2017 | Kim | A61B 5/4836 |
| 2018/0304101 A1* | 10/2018 | Yang | A61N 7/00 |

FOREIGN PATENT DOCUMENTS

| | | |
|---|---|---|
| JP | 2013-509958 A | 3/2013 |
| JP | 2014-515633 A | 7/2014 |
| JP | 2015-517350 A | 6/2015 |
| WO | 2008/139645 A1 | 11/2008 |
| WO | 2011/027264 A1 | 3/2011 |
| WO | 2011/057028 A1 | 5/2011 |
| WO | 2013/170223 A1 | 11/2013 |
| WO | 2015/192189 A1 | 12/2015 |
| WO | 2016/097867 A2 | 6/2016 |
| WO | 2016100353 A1 | 6/2016 |

OTHER PUBLICATIONS

Extended European Search Report in EP Application No. 18776558.1, dated Dec. 16, 2020, 8pp.

Office Action in JP application No. 2019-509409, dated May 31, 2022, 13pp.

Office Action in JP application No. 2022-183758, dated Nov. 7, 2023, 11pp.

* cited by examiner

EVALUATION OF WHITE MATTER LESIONS
RETENTION OF MYELIN SHEATH STRUCTURE BY LIPUS TREATMENT

EVALUATION OF WHITE MATTER LESIONS
INCREASE IN MATURE OLIGODENDROCYTES IN LIPUS-TREATED GROUP

EVALUATION OF HIPPOCAMPAL NERVE CELLS
INCREASE IN IMMATURE NEURONS IN LIPUS GROUP

ANGIOGENESIS
INCREASE IN HIPPOCAMPAL CAPILLARIES BY LIPUS TREATMENT

OLIGODENDROCYTE PRECURSOR CELLS

DEVICE FOR TREATING DEMENTIA, METHOD FOR OPERATING SAID DEVICE, AND PROGRAM

RELATED APPLICATIONS

The present application is a National Phase of International Application No. PCT/JP2018/013893 filed Mar. 30, 2018, which claims priority to Japanese Application No. 2017-067572, filed Mar. 30, 2017.

TECHNICAL FIELD

The present invention relates to a device for treating dementia, a method of operating the device, and a program.

BACKGROUND ART

At present, the number of dementia patients in Japan is said to be as many as about 2,600,000. Along with a burgeoning elderly population, the number of dementia patients is considered to also increase in the future, exceeding 3,000,000 in 2020. In addition, the number of dementia patients is estimated to be 35,000,000 worldwide, and according to a tentative calculation, is speculated to reach 65,000,000 in 2030, and 115,000,000 in 2050. In addition, as disease types of dementia, cerebrovascular dementia and Alzheimer's disease account for most of all dementias, and there are also many patients who exhibit symptoms of both thereof.

As measures against cerebrovascular dementia, drug treatment against hypertension, lipid metabolism abnormalities, or diabetes, and for example, alleviation of a lack of exercise, smoking, overeating, or stress have been performed. However, a pharmaceutical for treating cerebrovascular dementia itself has yet to be developed. In addition, for dementia of the Alzheimer's disease, pharmaceutical agents whose action mechanisms are activation of an acetylcholine pathway and inhibition of glutamic acid, and the like are commercially available, but treatment effects thereof have not always been sufficient. Therefore, development of effective means for treating dementia is desired.

The inventors of the present invention have previously confirmed angiogenesis and an improvement in left ventricular function in a porcine ischemic heart by low-intensity pulsed ultrasound (LIPUS) (Non-patent Literature 1). In recent years, the LIPUS has attracted widespread attention in, for example, the fields of orthopedics, gastroenterology, neurology, and dentistry, and has already been clinically performed for fracture treatment. However, there is no report that specifically verifies a treatment effect of irradiation with unfocused ultrasound energy on dementia.

CITATION LIST

Non-Patent Literature

NPL 1: Hanawa K. Shimokawa H, et al. PLoS One. 2014; 9: e104863

SUMMARY OF INVENTION

Technical Problem

An object of the present invention is to provide a novel method of treating dementia different from related-art drug treatment or the like.

Solution to Problem

Under the above-mentioned circumstances, the inventors of the present invention have found that dementia can be treated through angiogenesis and the like caused by propagating, to a wide range of the brain, unfocused ultrasound energy radiated from ultrasound probes so as to spread, instead of focused ultrasound energy radiated from ultrasound probes so as to be focused. The present invention is based on such novel finding.

Therefore, the present invention provides an ultrasound generator, a method of operating a device for treating dementia, and a program according to the following items:

Item 1. A device for treating dementia, including:
a plurality of ultrasound probes;
an ultrasound transducer arranged in each of the ultrasound probes and configured to propagate unfocused ultrasound energy to a brain; and
an ultrasound generator connected to each of the ultrasound probes.

Item 2. The device according to Item 1, wherein the unfocused ultrasound energy is diffused in an inversely tapered shape gradually enlarging in diameter toward a radiation direction.

Item 3. The device according to Item 2, wherein a spreading angle of an inclined surface of the unfocused ultrasound energy in the inversely tapered shape enlarging in diameter is from 50° to 100°.

Item 4. The device according to any one of Items 1 to 3, wherein the ultrasound generator is configured to control the ultrasound transducer so as to sequentially radiate the unfocused ultrasound energy between the plurality of ultrasound probes.

Item 5. The device according to Item 4, wherein unfocused ultrasound energy irradiation from the plurality of ultrasound probes is performed at an interval of 0.15/f ms or more, where f represents a frequency (MHz) of a pulse to be transmitted.

Item 6. The device according to any one of Items 1 to 5, wherein the plurality of ultrasound probes each further include an ultrasound receiving element for receiving ultrasound radiated from mutually different ultrasound probes and transmitted through the brain.

Item 7. The device according to Item 6, further including means for evaluating a treatment effect of ultrasound in accordance with a received intensity of the transmitted ultrasound.

Item 8. The device according to Item 6 or 7, further including output adjusting means for adjusting an output of ultrasound to be output in accordance with a received intensity of the transmitted ultrasound.

Item 9. A method of operating a device for treating dementia, the device including:
a plurality of ultrasound probes;
an ultrasound transducer arranged in each of the ultrasound probes and configured to propagate unfocused ultrasound energy to a brain; and
an ultrasound generator connected to each of the ultrasound probes,
the method including a step of causing the ultrasound transducer arranged in each of the ultrasound probes to generate unfocused ultrasound energy through control by the ultrasound generator.

Item 10. A program stored in a device for treating dementia, the device including:
  a plurality of ultrasound probes;
  an ultrasound transducer arranged in each of the ultrasound probes and configured to propagate unfocused ultrasound energy to a brain; and
  an ultrasound generator connected to each of the ultrasound probes,
  the program being configured to cause the device to execute a function of causing the ultrasound transducer arranged in each of the ultrasound probes to generate unfocused ultrasound energy through control by the ultrasound generator.

Item 11. A method of treating dementia, including a step of propagating unfocused ultrasound energy generated from an ultrasound transducer arranged in each of a plurality of ultrasound probes to a brain of a patient, through use of the ultrasound probes, an ultrasound transducer arranged in each of the ultrasound probes and configured to propagate unfocused ultrasound energy to the brain, and an ultrasound generator connected to each of the ultrasound probes.

Advantageous Effects of Invention

According to the present invention, through irradiation with unfocused ultrasound energy, the ultrasound energy can be propagated to a wide range of the brain, leading to angiogenesis, an increase in neurons, and the like, and thus cognitive dysfunction can be treated. Accordingly, according to the present invention, the novel method of treating dementia different from related-art drug treatment or the like can be provided.

DESCRIPTION OF EMBODIMENTS

Device for Treating Dementia

The invention of the present application is described below with reference to the drawings. The present invention provides a device for treating dementia, including: a plurality of ultrasound probes; an ultrasound transducer arranged in each of the ultrasound probes and configured to propagate unfocused ultrasound energy to a brain; and an ultrasound generator connected to each of the ultrasound probes.

Herein, the "device for treating dementia" is sometimes referred to simply as dementia treatment device. In the present invention, the "dementia" includes cerebrovascular dementia, Alzheimer's disease, symptoms indicating both thereof, and the like. In addition, in the present invention, the term "dementia" also encompasses symptoms such as mild cognitive impairment.

Figure 1:
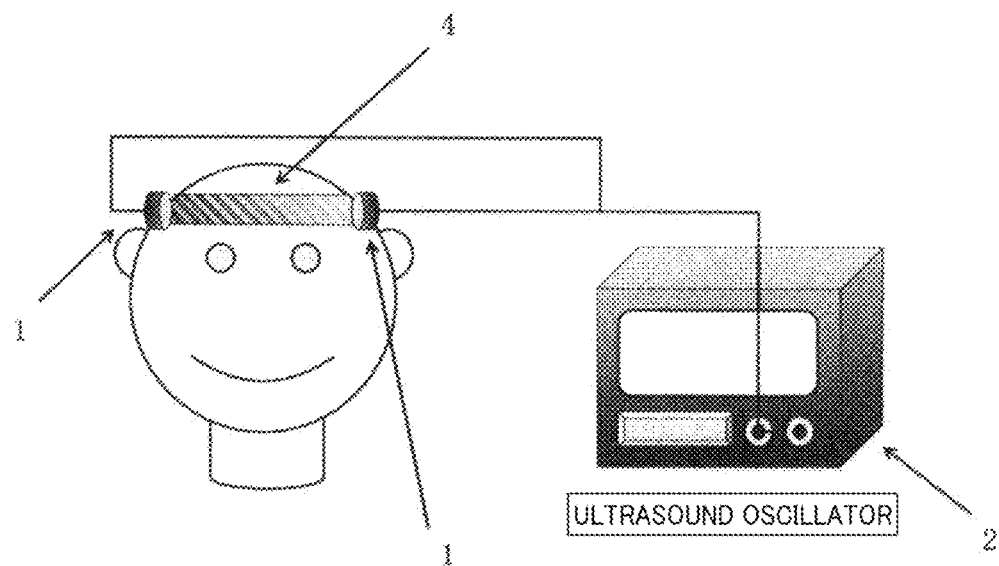
FIG. 1 is a schematic view of a device according to a typical embodiment of the present invention.
Figure 2:
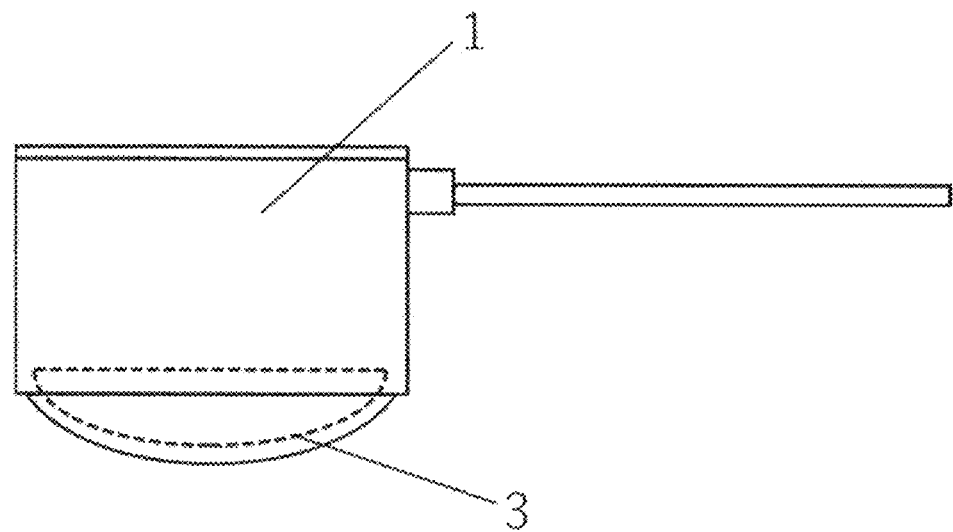
FIG. 2 is a cross-sectional schematic view of an ultrasound probe.

FIG. 1 is a schematic view of a device according to a typical embodiment of the present invention. As illustrated in FIG. 1, the dementia treatment device of the present invention includes a plurality of ultrasound probes 1 and an ultrasound generator 2 connected to each of the ultrasound probes 1. FIG. 2 is a schematic view of the ultrasound probe. An ultrasound transducer 3 configured to propagate unfocused ultrasound energy to a brain is arranged in each of the ultrasound probes. In the present invention, as illustrated in FIG. 2, a single ultrasound transducer 3 is typically arranged for one ultrasound probe 1. Electricity is transmitted from the ultrasound generator 2 to the ultrasound transducer 3 through wiring or the like (not shown) to apply a voltage thereto, and thus the ultrasound transducer 3 vibrates. The frequency, time period, timing, and the like of the vibration of the ultrasound transducer 3 are controlled by the ultrasound generator 2. In addition, the same ultrasound transducer 3 may be caused to act as an ultrasound receiving element by switching control signals from the ultrasound generator 2.

In the present invention, when the ultrasound irradiation surface of one ultrasound transducer is caused to have a convexly curved shape, or a plurality of ultrasound transducers are arranged in a convexly curved shape, so that the direction of ultrasound may be an unfocused direction, the unfocused ultrasound energy can be efficiently propagated to the brain, and as a result, dementia can be treated through activation of nerve cells by angiogenesis in the hippocampus and enhancement of the activity of oligodendrocyte precursor cells in the corpus callosum and the accompanying reduction in white matter lesions.

Figure 3:
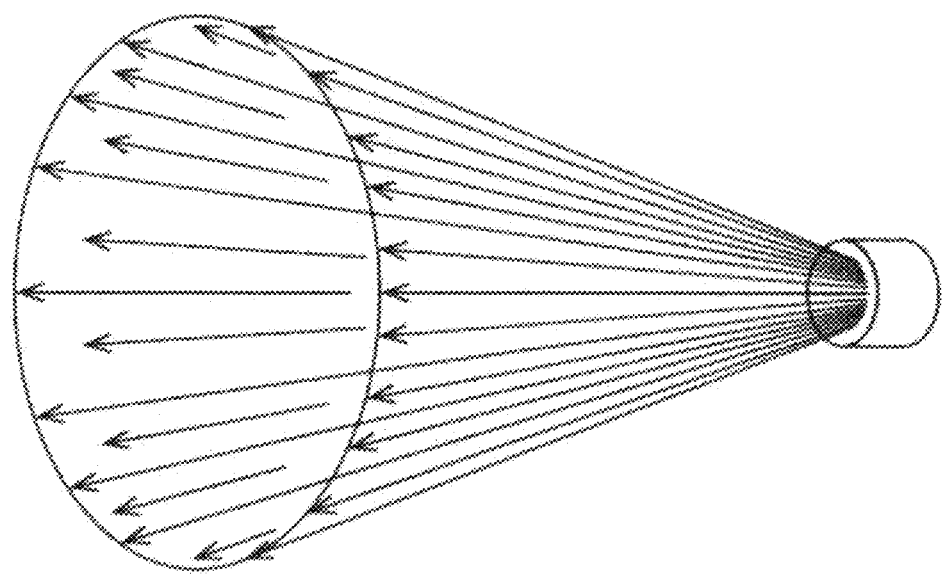
FIG. 3 is a schematic view of ultrasound energy diffusion in one embodiment of the present invention.
Figure 4:
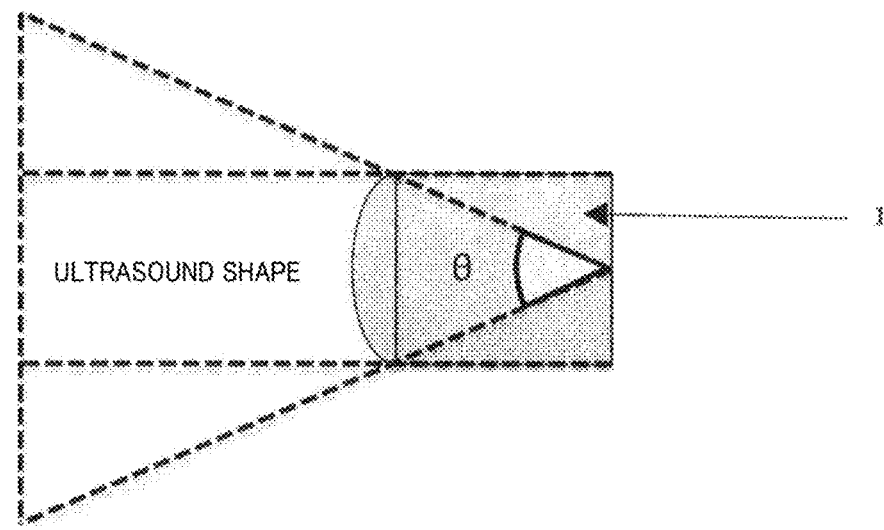
FIG. 4 is a side view of an ultrasound probe 1 in an embodiment in which diffusion occurs in an inversely tapered shape gradually enlarging in diameter toward a radiation direction.
Figure 5:
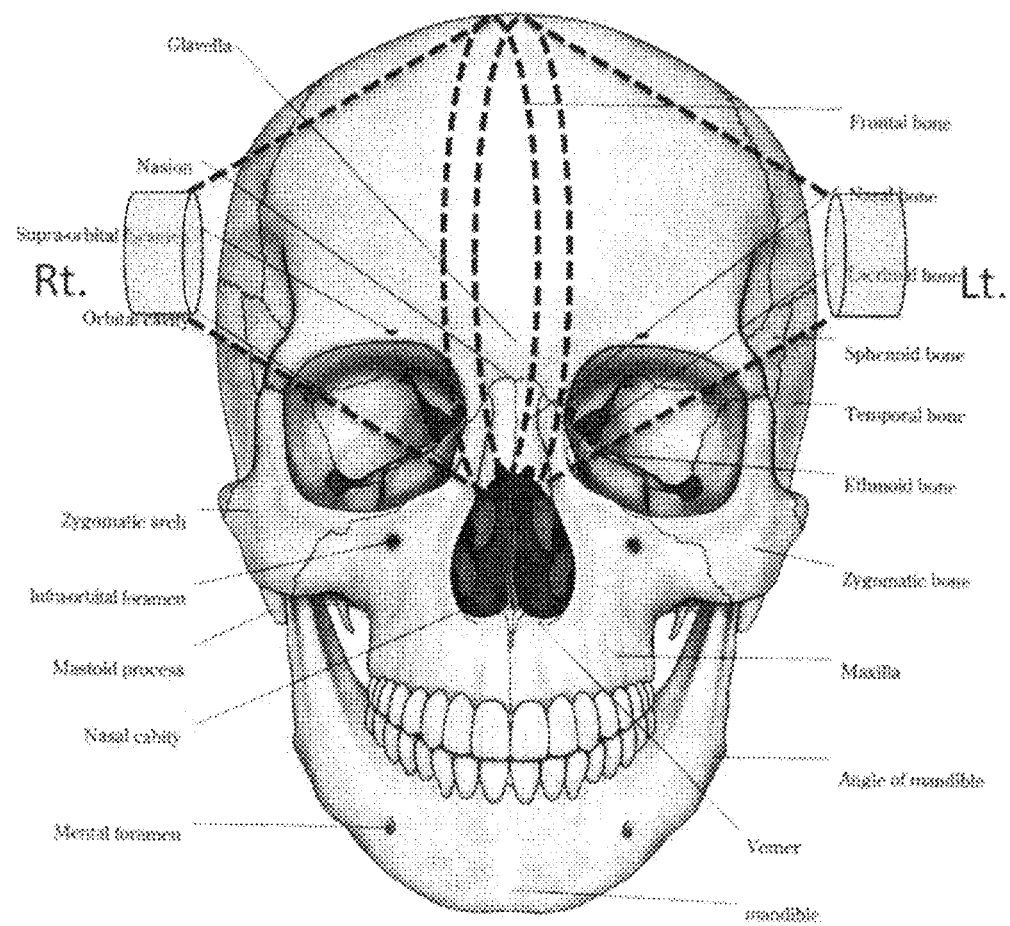
FIG. 5 is a schematic view of an embodiment in which two ultrasound probes are arranged on temporal regions.

In the present invention, the unfocused ultrasound energy means ultrasound energy that is diffused without focusing on one point or one line. In the present invention, the unfocused ultrasound energy is preferably diffused in an inversely tapered shape gradually enlarging in diameter toward a radiation direction. The spreading angle of the inclined surface of the unfocused ultrasound energy in the inversely tapered shape enlarging in diameter is preferably from 50° to 100°, more preferably from 60° to 90°. As illustrated in FIG. 3, ultrasound energy is typically diffused in an approximately conical shape (the bottom surface portion may be a curved surface). A side view of the ultrasound probe 1 in an embodiment in which diffusion occurs in the inversely tapered shape gradually enlarging in diameter toward the radiation direction is illustrated in FIG. 4. In the present invention, the spreading angle of the inclined surface of the unfocused ultrasound energy in the inversely tapered shape enlarging in diameter means θ in FIG. 4. In a typical embodiment, two ultrasound probes 1 are preferably arranged in temporal regions (FIG. 5). This is preferred because, consequently, as described above, through the diffusion of the unfocused ultrasound energy in the inversely tapered shape, the ultrasound energy can be propagated to most of the brain, for example, portions including at least the hippocampus and the corpus callosum, typically the entire brain (FIG. 5).

In the present invention, from the viewpoint of promoting angiogenesis, an increase in neurons, and the like with gentle ultrasound stimulation, the amplitude (acoustic pressure) of the radiated ultrasound preferably has a low intensity of, for example, 3.0 MPa or less, more preferably 0.7 MPa or less. Meanwhile, in the present invention, the lower limit of the intensity of the radiated ultrasound is not particularly limited, but from the viewpoint of the effectiveness of the treatment, is preferably, for example, 0.1 MPa or more, more preferably 0.2 MPa or more. In the present invention, the intensity of the ultrasound the frequency of the radiated ultrasound is not particularly limited, but may be appropriately set within the range of, for example, from 0.5 MHz to 1.5 MHz, preferably from 0.5 MHz to 1.0 MHz.

In the present invention, a material for the ultrasound transducer is not particularly limited as long as the material can generate the above-mentioned unfocused ultrasound energy, but examples thereof include resins (e.g., a NORYL resin, polyacetal, an ionomer resin, and a urethane resin) and metals (e.g., a copper alloy). In addition, the size of a portion of each of the ultrasound probes that generates ultrasound is not particularly limited, but for example, when the shape of the portion that generates ultrasound is an approximately circular shape, its diameter is preferably from 1.0 cm to 5.0 cm, more preferably from 2.0 cm to 4.0 cm. In addition, the shape of the portion of each of the probes that generates ultrasound is not particularly limited, and may be appropriately designed to be, for example, an approximately circular shape, an approximately elliptical shape, or a polygonal shape (e.g., a triangle, a quadrilateral (e.g., a square, a rectangle, a parallelogram, or a trapezoid), a pentagon, a hexagon, a heptagon, or an octagon). In addition, the dimensions thereof may also be appropriately set to, for example, such dimensions as to correspond to those described above for the approximately circular shape so that the ultrasound may be propagated to a wider region of the brain.

In addition, in the present invention, when the plurality of ultrasound probes are used to radiate unfocused ultrasound energy from different sites of the head, ultrasound can be propagated to a wider range of the brain. In the present invention, from the viewpoint of safety, more specifically from the viewpoint of suppressing the propagation of excessive ultrasound energy into the brain as a result of overlapping propagation of ultrasound energy radiated from a plurality of sites into the brain, it is preferred that the ultrasound generator control the ultrasound transducer so as to sequentially radiate unfocused ultrasound energy between the plurality of ultrasound probes. In the present invention, to sequentially radiate unfocused ultrasound energy between the plurality of ultrasound probes means that, of the plurality of ultrasound probes, ultrasound is generated from only one ultrasound probe in the same time period, i.e., ultrasound is not simultaneously generated from two or more ultrasound probes as follows: first, ultrasound is generated from one ultrasound probe out of the plurality of ultrasound probes, during which ultrasound is not generated from any other ultrasound probe, and next, ultrasound is generated from another ultrasound probe, during which ultrasound is not generated from any other ultrasound probe In the present invention, the ultrasound generated from each of the ultrasound probes is transmitted through the skull to be propagated to the brain, and is reflected by the skull on the side opposite to where the ultrasound probe is arranged, to be propagated again in the direction of the ultrasound probe. Then, the reflected ultrasound is reflected again by the skull on the side where the ultrasound probe is arranged, to be propagated. During this, the ultrasound is attenuated when propagated in the brain and when reflected by the skull. Thus, the ultrasound generated from each of the ultrasound probes reciprocates in the brain a plurality of times while being attenuated every time the ultrasound is reflected by the skull.

Therefore, in the present invention, when unfocused ultrasound energy is sequentially radiated between the plurality of ultrasound probes, it is preferred that there be an interval at which ultrasound is generated from the plurality of ultrasound probes so as to prevent excessive ultrasound stimulation even when the radiated wave or reflected wave of unfocused ultrasound energy generated from one ultrasound probe is attenuated and overlaps unfocused ultrasound energy generated from the next ultrasound probe. From the above-mentioned viewpoint, in the present invention, the unfocused ultrasound energy irradiation with the plurality of ultrasound probes is performed at an interval of preferably 0.15/f (f represents the frequency (MHz) of a pulse to be transmitted) ms or more, more preferably 0.30/f ms or more. In addition, from the viewpoint of obtaining a higher treatment effect in a short period of time, the unfocused ultrasound energy irradiation with the plurality of ultrasound probes is performed at an interval of preferably 0.60/f (f (MHz) is as described above) ms or less, more preferably 0.30/f ms or less. In the present invention, the frequency means the frequency of transmitted ultrasound.

Figure 6:
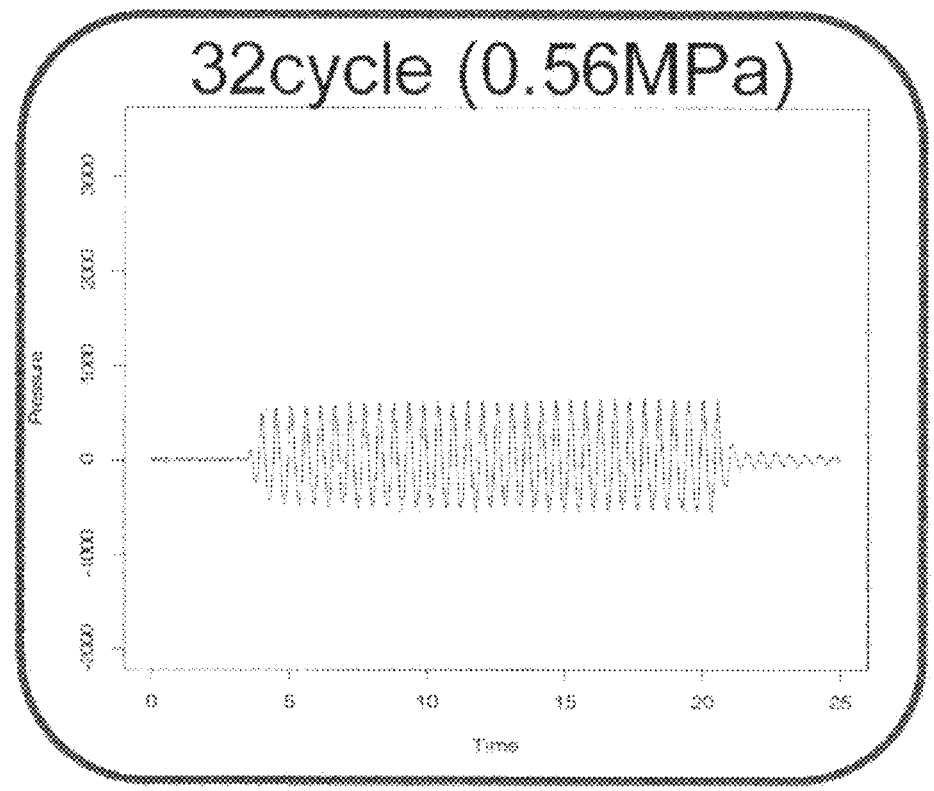
FIG. 6 is a graph for showing the waveform of ultrasound in one embodiment.

Herein, the interval of the unfocused ultrasound energy irradiation means, unless otherwise specified, a period of time from the end of ultrasound irradiation from one ultrasound probe to the start of ultrasound irradiation from the next ultrasound probe for the above-mentioned reason when irradiation is performed by starting ultrasound irradiation from one ultrasound probe, ending ultrasound irradiation from the ultrasound probe, starting ultrasound irradiation from the next ultrasound probe, ending ultrasound irradiation from the next ultrasound probes In the present invention, the radiated ultrasound is a non-continuous wave, and the number of cycles thereof is not particularly limited, but may be appropriately set within the range of, for example, from 1 cycle to 64 cycles, preferably from 24 cycles to 40 cycles. Herein, the number of cycles of ultrasound refers to the number of cycles within a width from the start of ultrasound irradiation to the end of ultrasound irradiation (herein sometimes referred to as pulse width). For example, in the case of ultrasound having a waveform shown in FIG. 6, the number of cycles is 32 cycles. A treatment time with ultrasound is not particularly limited, but for example, may be appropriately set within the range of from 1 minute to 60 minutes, preferably from 15 minutes to 25 minutes per treatment depending on symptoms of a patient, the intensity of the ultrasound, and the like. In addition, the number of times of the treatment per day is also not particularly limited, but may be appropriately set within the range of, for example, from 1 to 4, preferably from 2 to 3. In addition, a frequency at which the treatment is performed is also not particularly limited, and may be appropriately set within the range of, for example, from 1 time to 7 times, preferably from 2 times to 3 times a week. A treatment interval is also not particularly limited, and for example, when one set of treatment involves performing the treatment at the above-mentioned frequency for from 5 days to 10 days (more preferably from 6 days to 8 days), the treatment is preferably performed continually at an interval of once in 1 month to 4 months (e.g., once in 1 month to 3.5 months) unless there is an adverse event or the like.

Figure 7:
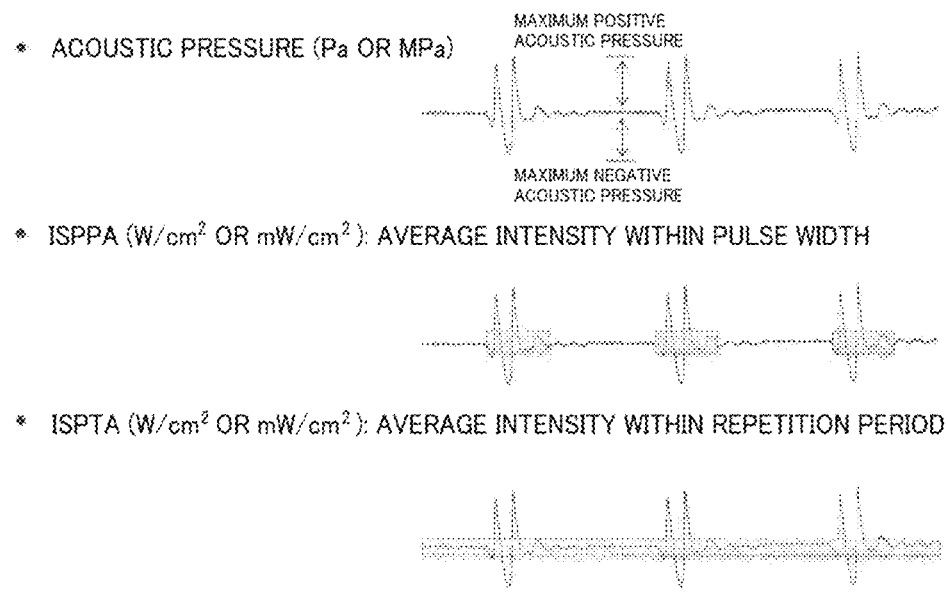
FIG. 7 is an explanatory diagram of ISPPA and ISPTA.

The intensity of the ultrasound may be adjusted on the basis of ISPPA, ISPTA, or the like. Herein, the ISPPA refers to an average intensity within a pulse width. The ISPTA refers to an average intensity within a repetition period. In FIG. 7, the ISPPA and ISPTA of ultrasound are illustrated.

In addition, the ISPTA of the radiated ultrasound is not particularly limited, but from the viewpoint of promoting angiogenesis, an increase in neurons, and the like with gentle ultrasound stimulation, may be appropriately set within the range of, for example, 720 $mW/cm^2$ or less, preferably from 100 $mW/cm^2$ to 150 $mW/cm^2$. When a plurality of ultrasound probes are used, the ISPTA is expressed as the sum of the ISPTAs of radiated ultrasound of the ultrasound probes. In addition, in the present invention, the duty ratio (DutyCycle) of the radiated ultrasound is not particularly limited, but may be appropriately set within the range of, for example, from 0.1% to 50%, preferably from 0.1% to 20%.

Herein, the duty ratio refers to the ratio of the irradiation time of ultrasound in the period of time of one cycle involving radiating ultrasound for a certain period of time and pausing ultrasound irradiation for a certain period of time. In other words, the duty ratio refers to the ratio of the irradiation time of ultrasound to [irradiation time of ultrasound+irradiation pause time] in one cycle. When a plurality of ultrasound probes are used, the duty ratio is expressed as the sum of the duty ratios of radiated ultrasound of the ultrasound probes.

In addition, as described later, ultrasound generated from the ultrasound probes is significantly attenuated when transmitted through the skull. In addition, the degree of the attenuation varies depending on the thickness of the skull through which the ultrasound is transmitted. Therefore, it is preferred that, by inputting the thickness of the skull into the ultrasound generator on the basis of, for example, a head CT image taken at the time of the diagnosis of dementia, an estimated value of appropriate output be calculated by the device on the basis of the numerical value of the thickness of the skull, and be emitted as ultrasound for treatment. In such embodiment, the ultrasound generator includes means for inputting the numerical value of the thickness of the skull, and calculation means for calculating the estimated value of appropriate output from the input value.

In addition, in the present invention, it is preferred that the plurality of ultrasound probes each further include an ultrasound receiving element for receiving ultrasound radiated from mutually different ultrasound probes and transmitted through the brain. An embodiment including such receiving element is preferred because whether or not the intensity of ultrasound emitted from each of the ultrasound probes and transmitted through the brain falls within a range assumed in advance can be monitored. Its own transmitted ultrasound may be received and used. As described above, the ultrasound transducer may be used also as a receiving element by switching control signals from the ultrasound generator. Therefore, in the present invention, the device in which "the plurality of ultrasound probes each further include an ultrasound receiving element for receiving ultrasound radiated from mutually different ultrasound probes and transmitted through the brain" also encompasses a device in which the ultrasound probes each include an ultrasound transducer, and the ultrasound transducer is used also as a receiving element. In such embodiment, for example, it is appropriate to use the ultrasound transducer arranged in part of the plurality of ultrasound probes (e.g., one of the ultrasound probes) as a receiving element, and to use the ultrasound transducer arranged in any other ultrasound probe as an emitting element. In addition, at least part of a plurality of ultrasound transducers may be used by being switched between an emitting element and a receiving element after a lapse of a certain period of time.

In addition, it is preferred that the device further include means for evaluating a treatment effect of ultrasound in accordance with a received intensity of the transmitted ultrasound. For example, by such means, the integrated value of the intensity of the received ultrasound may be calculated to perform: the evaluation of a treatment effect using the integrated value as an indicator; the evaluation that treatment having a certain effect has ended when the integrated value has reached a predetermined value; or the like.

In addition, it is preferred that the device further include output adjusting means for adjusting an output of ultrasound to be output in accordance with a received intensity of the transmitted ultrasound. More specifically, an example of the output adjusting means is feedback means (processor) for decreasing output when the acoustic pressure of ultrasound received by the receiving element is equal to or higher than a predetermined value.

A standard value for decreasing output when the intensity of ultrasound energy received by the receiving element is equal to or higher than a predetermined value is not particularly limited, but in consideration of a safety standard and the like, may be appropriately set to, for example, an acoustic pressure of 0.1 MPa or less, preferably 0.05 MPa or less. In a preferred embodiment of the present invention, the following setting may be made in advance: output is decreased when the receiving element receives ultrasound having an intensity exceeding an upper limit value set within the above-mentioned range. In addition, the device of the present invention may include, for example, a document in which a procedure for performing a method of operating the device or treatment method of the present invention to be described later is written.

Method of Operating Device for Treating Dementia and Method of Treating Dementia The present invention also provides a method of operating a device for treating dementia, the device including: a plurality of ultrasound probes; an ultrasound transducer arranged in each of the ultrasound probes and configured to propagate unfocused ultrasound energy to a brain; and an ultrasound generator connected to each of the ultrasound probes, the method including a step of causing the ultrasound transducer arranged in each of the ultrasound probes to generate unfocused ultrasound energy through control by the ultrasound generator.

Figure 8:
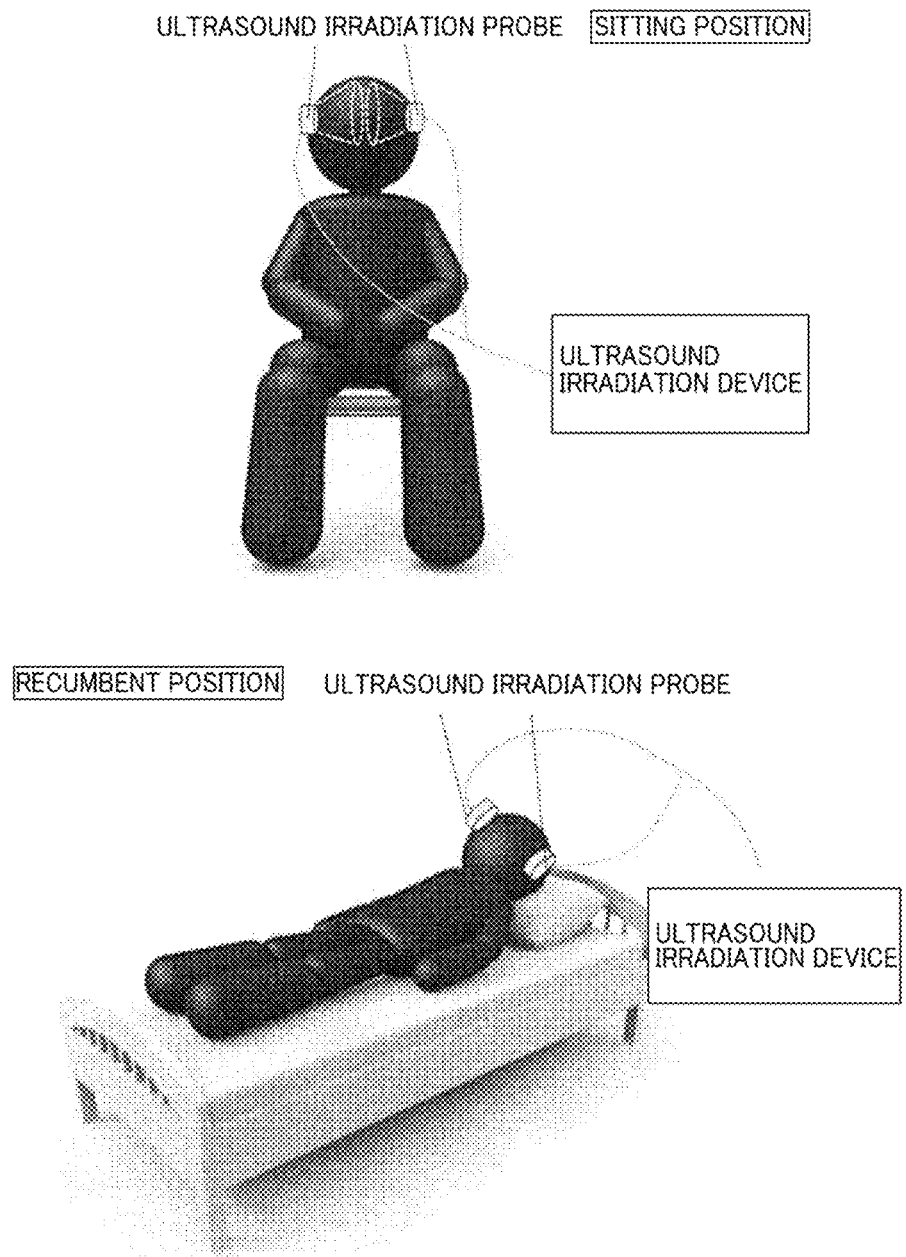
FIG. 8 is a schematic view of a method according to an embodiment of the present invention (posture of a subject). Top of FIG. 8: The subject is in a sitting position and actually wearing a fixing headband for fixing probes. Bottom of FIG. 8: The subject is in a recumbent position and actually wearing a fixing headband for fixing probes.

In a typical embodiment, as illustrated in FIG. 1, the method of the present invention is performed under a state in which the ultrasound probes 1 are brought into contact with the head. Sites with which the ultrasound probes 1 are brought into contact are not particularly limited, but the ultrasound probes 1 are preferably brought into contact with temporal regions (temples) because the skull is relatively thin to facilitate the propagation of ultrasound to the brain. A gel may be appropriately applied to the ultrasound generation portions of the ultrasound probes 1 and/or the portions of the head with which the ultrasound probes are brought into contact so that ultrasound may be efficiently propagated to the brain. In addition, as illustrated in FIG. 1, the ultrasound probes 1 may be fixed with a headband 4. In addition, as illustrated in FIG. 8, the posture of a subject may be a sitting position, or may be a recumbent position. In addition, examples of the subject to be subjected to the method of the present invention include mammals, such as mice, rats, humans, monkeys, dogs, and pigs. Of those, humans are preferred.

The present invention also provides a method of treating dementia, including a step of propagating unfocused ultrasound energy generated from an ultrasound transducer arranged in each of a plurality of ultrasound probes to a brain of a patient, through use of the ultrasound probes, an ultrasound transducer arranged in each of the ultrasound probes and configured to propagate unfocused ultrasound energy to the brain, and an ultrasound generator connected to each of the ultrasound probes.

For the device to be used for those methods of the present invention, irradiation conditions of the ultrasound, and the like, ones similar to those described above in the "Device for Treating Dementia" section may be adopted.

Program

The present invention provides a program stored in a device for treating dementia, the device including: a plurality of ultrasound probes; an ultrasound transducer arranged in each of the ultrasound probes and configured to propagate unfocused ultrasound energy to a brain; and an ultrasound generator connected to each of the ultrasound probes, the program being configured to cause the device to execute a function of causing the ultrasound transducer arranged in each of the ultrasound probes to generate unfocused ultrasound energy through control by the ultrasound generator.

The program of the present invention may be used to cause the device for treating dementia described above (a computer included in the device) to generate unfocused ultrasound energy. In addition, in an embodiment in which, in the device of the present invention, the plurality of ultrasound probes each further include an ultrasound receiving element for receiving ultrasound radiated from mutually different ultrasound probes and transmitted through the brain, the program of the present invention may cause the device to execute a function of evaluating a treatment effect of ultrasound in accordance with the received intensity of the transmitted ultrasound. For example, the program may cause the device to evaluate whether the treatment effect is high or low by calculating the integrated value of the intensity of the received ultrasound, and comparing the integrated value as an indicator to a value set in advance. In addition, the program may cause the device to calculate the integrated value of the intensity of the received ultrasound and evaluate that treatment having a certain effect has ended when the integrated value has reached a predetermined value set in advance. In addition, in such embodiment, the device may include a display portion for such evaluation. In this case, the program of the present invention may cause the device (computer) to execute a function of displaying the evaluation obtained as described above on the display portion. Further, in such embodiment, the program of the present invention may cause the device (computer) to execute an output adjusting function of adjusting the output of ultrasound to be output in accordance with the received intensity of the transmitted ultrasound. More specifically, the program causes, for example, feedback means (processor) for decreasing output to execute output adjustment when the acoustic pressure of the ultrasound received by the receiving element is equal to or higher than a predetermined value.

The present invention has been described above with reference to the drawings in which specific embodiments are illustrated. However, it is evident that the present invention is not limited to those embodiments. For example, connection between each of the ultrasound probes and the ultrasound generator may be wired as illustrated in FIG. 1, or may be wireless. Also with regard to the number of ultrasound probes, a description has been made by way of the embodiment in which two ultrasound probes are used, but three or more ultrasound probes may be used. For example, ultrasound irradiation may be performed with two ultrasound probes brought into contact with both temporal regions (temples), and another ultrasound probe brought into contact with a boundary portion (foramen magnum) between the occiput and the nape.

EXAMPLES

The present invention is exemplified below by way of specific Examples, but the present invention is not limited to these Examples.

Example 1 Verification of Dementia Treatment Effect of Ultrasound Treatment

Example 1-1 Vascular Dementia Model (Bilateral Common Carotid Artery Stenosis (BCAS) Model)

In subcortical vascular dementia, which accounts for a majority of vascular dementias, chronic cerebral ischemia is considered to be an important pathological mechanism. In a BCAS model, when cerebral ischemia continues for a long period of time, white matter lesions similar to those in humans are formed to cause higher dysfunction. Accordingly, the BCAS model is the most standard vascular dementia model at present. Therefore, in this Example, the entire brain of such BCAS model was subjected to ultrasound irradiation to verify a treatment effect on dementia.

Specifically, the BCAS model was generated by treating 9- to 12-week-old C57Bl/6 male mice (n=10 to 15) by a method described in the literature (Shibata M, et al. Stroke. 2004 November; 35(11):2598-603). As a sham group, 9- to 12-week-old C57Bl/6 male mice without the BCAS treatment were used.

Ultrasound irradiation was performed 3 times in 1 week after BCAS operation (1 day, 3 days, and 5 days after BCAS operation). The ultrasound irradiation was performed for 20 minutes 3 times per day.

A laser speckle device (manufactured by OMEGAWAVE, OMEGAZONE mini2) was used to measure the degree of cerebral blood flow (CBF) of each of a BCAS preoperative group, a 1-day group, a 2-day group, a 4-day group, a 7-day group, and a 28-day group. In addition, various kinds of immunostaining (immunofluorescence staining) using brain tissue specimens, expression analysis using Western blotting of proteins, gene expression analysis using RNA-sequencing, and the like were performed.

Irradiation conditions were as described below, and irradiation was performed with rectangular ultrasound probes each having an area of 3.75 cm$^2$ (1.5 cm×2.5 cm) so that ultrasound was propagated to the entire brain of the model.

Figure 9:
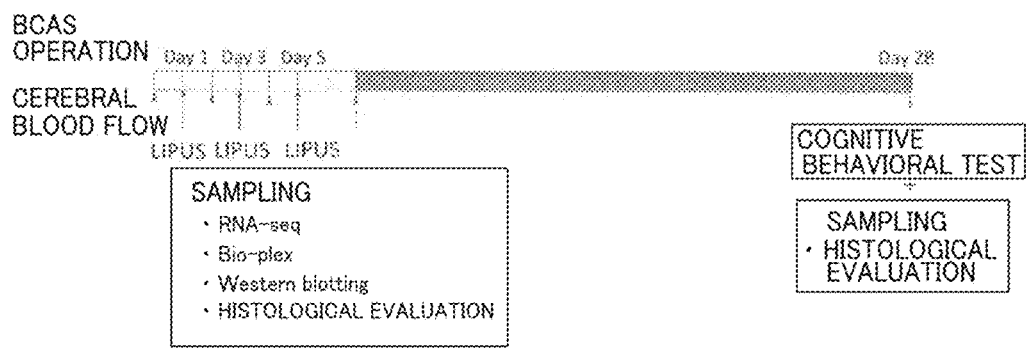
FIG. 9 is a schematic view of a test method of Example 1-1. •Irradiation is performed 3 times every other day for 1 week after BCAS operation: 20 minutes×3 times/day. •The degrees of cerebral blood flow (CBF) of groups are compared using a laser speckle device. •A cognitive behavioral test is performed on Day 28 after operation. •Sampling for histological/biochemical analyses is performed on each of Days 3, 7, and 28.
Figure 9:
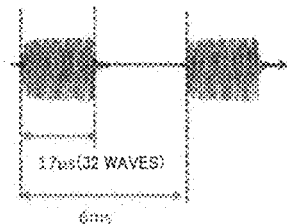
Figure 10:
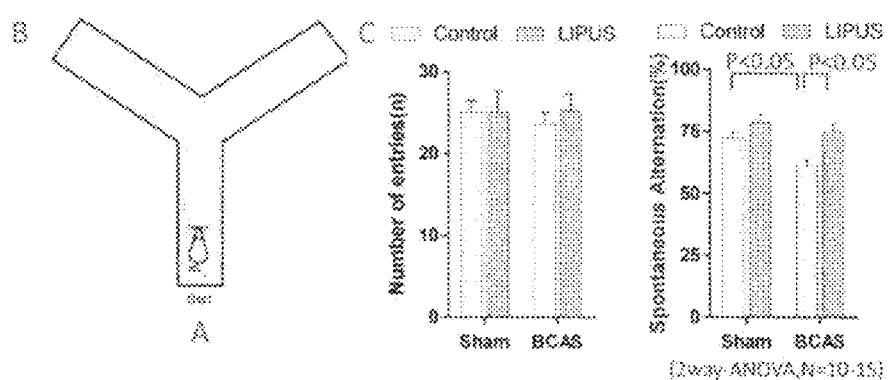
FIG. 10 are the outline of Example 1-1 and graphs for showing results thereof. Cognitive behavioral test: for suppression of cognitive dysfunction by LIPUS treatment. Results of a Y-maze test (method of evaluating cognitive function through utilization of the behavior of a mouse of choosing a path different from that the mouse has come down like A→B→C when having no/mal cognitive function)

Irradiation Conditions:
 Intensity (ISPTA): 100 mW/cm$^2$
 Frequency: 1.875 MHz
 Number of cycles: 32 cycles
 Repetition frequency: 6 kHz The outline of this test is illustrated in FIG. 9. The results of a cognitive behavioral test are shown in FIG. 10. In FIG. 10, Number of entries represents the total number of entries into arms, and Spontaneous Alternation represents the spontaneous alternation of mice ([number of three consecutive entries into different arms]/[number of entries into all arms of Y-maze −2]). The ultrasound treatment significantly suppressed cognitive dysfunction in the cognitive behavioral test.

Evaluation of White Matter Lesions (Corpus Callosum)

Figure 11:
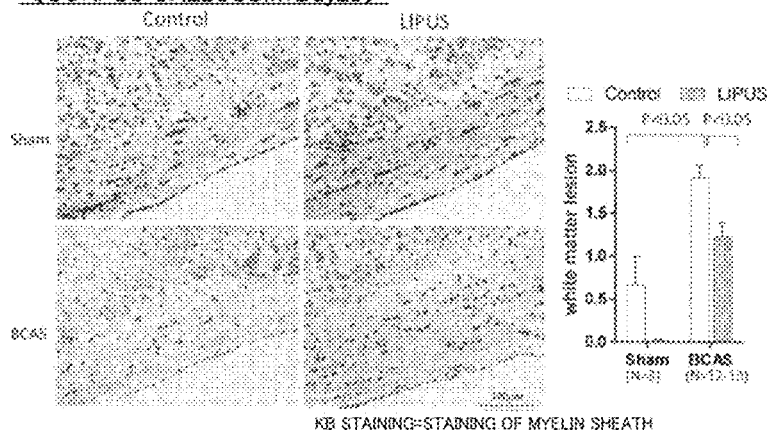
FIG. 11 are images and graphs for showing results of Example 1-1.
Figure 11:
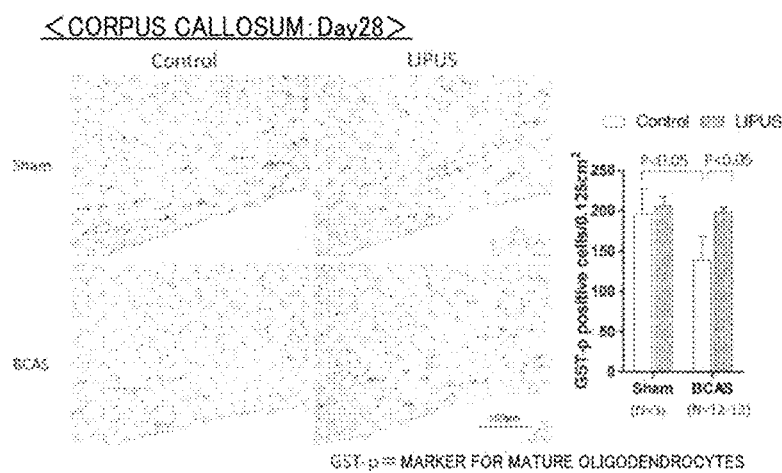
Figure 12:
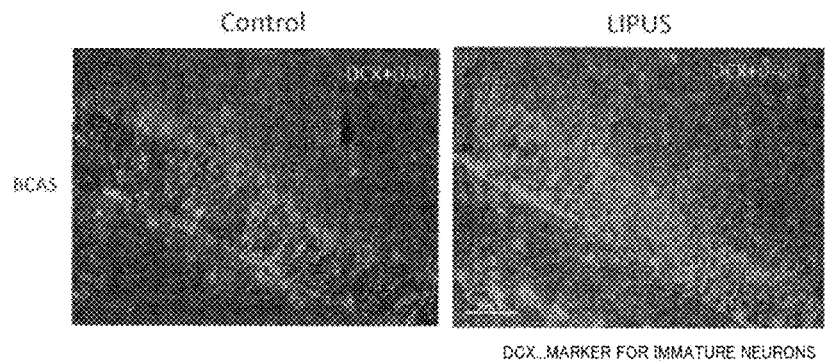
FIG. 12 are images and a graph for showing results of Example 1-1.
Figure 12:
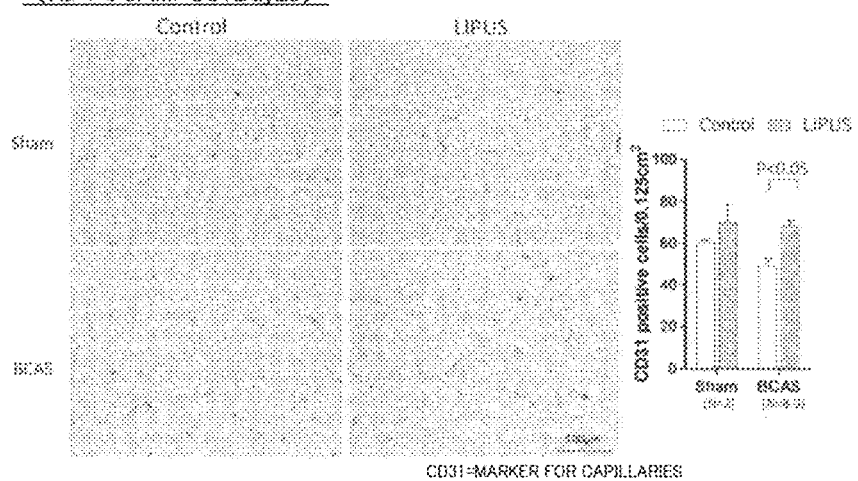

As shown in FIG. 11, the ultrasound treatment significantly retained the myelin sheath structure, and also increased the number of mature oligodendrocytes forming the myelin sheath. On the left of FIG. 11 under the caption "retention of brain sheath structure by LIPUS treatment," KB stained images of the corpus callosum are shown. In the graph on the right thereof in FIG. 11, white matter lesion represents the degree of demyelinated lesions of white matter in the corpus callosum. On the left of FIG. 11 under the caption "increase in mature oligodendrocytes in LIPUS-treated group," GST-p immunostained images of the corpus callosum are shown. In the graph on the right thereof in FIG. 11, the number of GST-p positive cells on the vertical axis represents the number of mature oligodendrocytes per unit area. As shown in FIG. 11, the ultrasound treatment significantly retained the myelin sheath structure, and also increased the number of mature oligodendrocytes forming the myelin sheath. Under the caption "increase in immature neurons in LIPUS group" in the top of FIGS. 12, DCX immunofluorescence stained images are shown. On the left of the bottom of FIG. 12 under the caption "increase in hippocampal capillaries by LIPUS treatment," CD31 immunostained images of the hippocampus are shown. In the graph on the right thereof in the bottom of FIG. 12, the number of CD31 positive cells on the vertical axis represents the number of capillaries per unit area. As shown in FIG. 12, in the hippocampus, immature neurons were increased, and capillaries were also increased.

Figure 13:
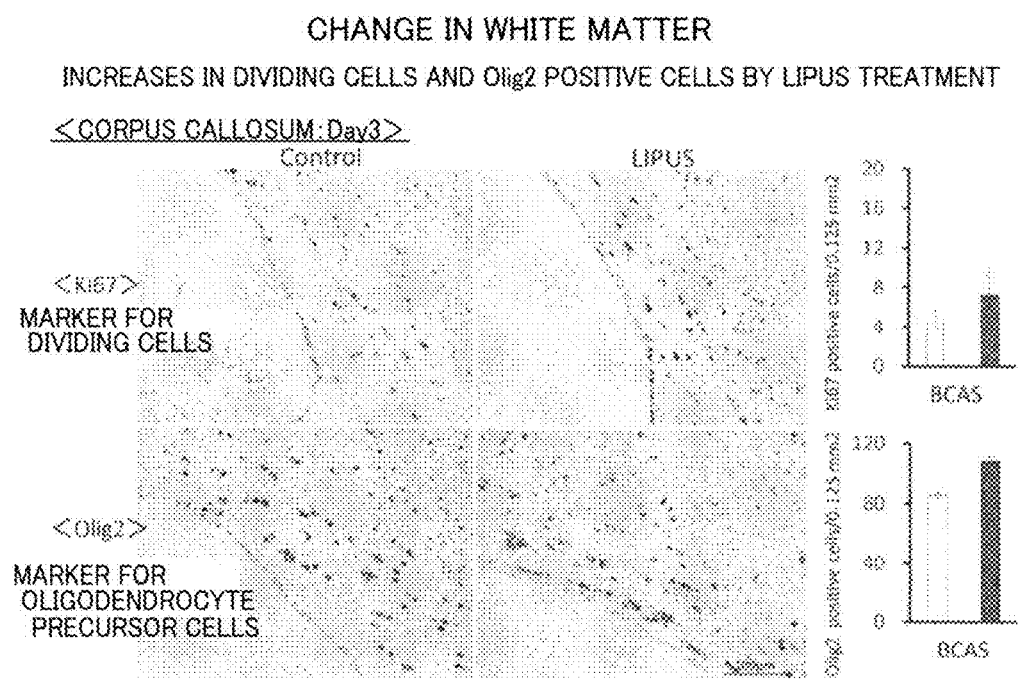
FIG. 13 are images and graphs for showing results of Example 1-1.

A Ki67 immunostained image is shown in the top left of FIG. 13, and an Olig2 immunostained image is shown in the bottom left thereof. In the graphs on the right of FIG. 13, the number of Ki67 positive cells and the number of Olig2 positive cells on the vertical axis represent the number of cells undergoing cell division and the number of oligodendrocyte precursor cells, respectively. Therefore, FIG. 13 were obtained in the evaluation of an acute-phase tissue, and the ultrasound treatment tended to increase growing cells in the corpus callosum, and also increased Olig2 positive cells. In view of this, whether the dividing/growing cells were oligodendrocyte precursor cells was confirmed by double fluorescent immunostaining, and as a result, they were certainly merged, revealing that the dividing/growing cells were oligodendrocyte precursor cells (OPCs). Gene exhaustive analysis using RNA-sequencing also confirmed changes in genes associated with the differentiation and growth of oligodendrocytes, such as Olig2.

Figure 14:
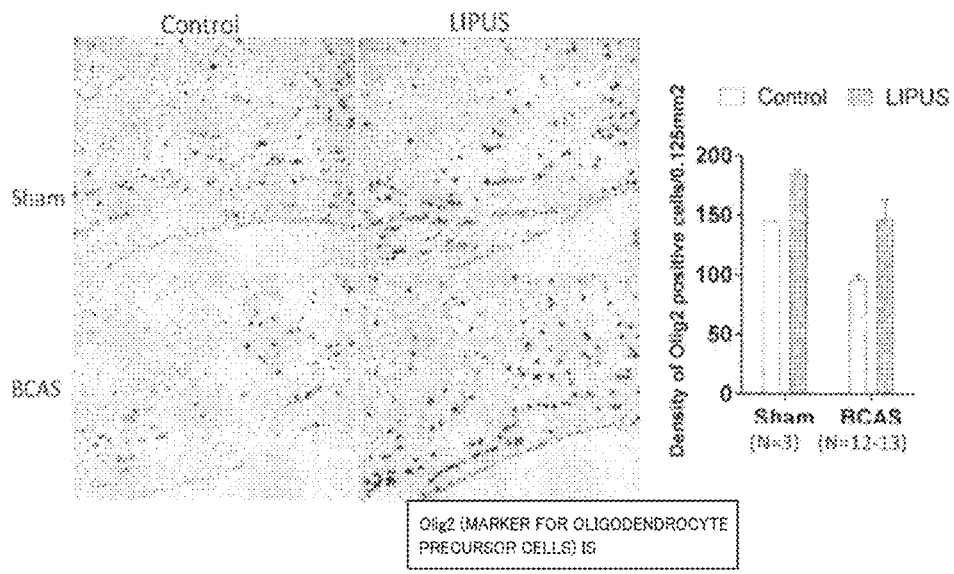
FIG. 14 are images and a graph for showing results of Example 1-1. There are more oligodendrocyte precursor cells than in a non-treated group even at one month after operation.
Figure 15:
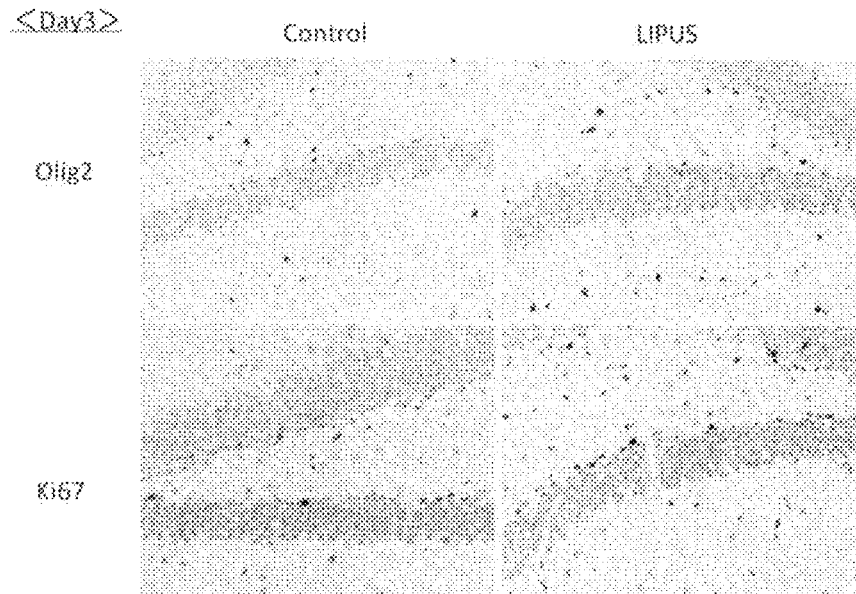
FIG. 15 are images for showing results of Example 1-1 (evaluation of OPCs and dividing cells). Both tend to increase through LIPUS treatment.

In addition, Olig2 immunostained images in the corpus callosum are shown on the left of FIG. 14. In the graph on the right of FIG. 14, the number of Olig2 positive cells on the vertical axis represents the number of oligodendrocyte precursor cells 28 days after operation. Therefore, as shown in FIG. 14, the OPCs were significantly increased in the ultrasound-treated group even at one month after operation, suggesting the persistence of the effect. In addition, in FIG. 15, Olig2 immunostained images and Ki67 immunostained images of the hippocampus at 3 days after operation are shown. As shown in FIG. 15, also in the hippocampus, Olig2 positive cells and Ki67 positive cells tended to be increased, and the results did not contradict the results of FIG. 11 for evaluation at 1 month after operation. Thus, it was suggested that the growth of OPCs in the corpus callosum, and the angiogenesis and immature neuron increase in the hippocampus influenced the improvement of cognitive function.

Example 1-2 Alzheimer's Disease Model (Transgenic)

Figure 16:
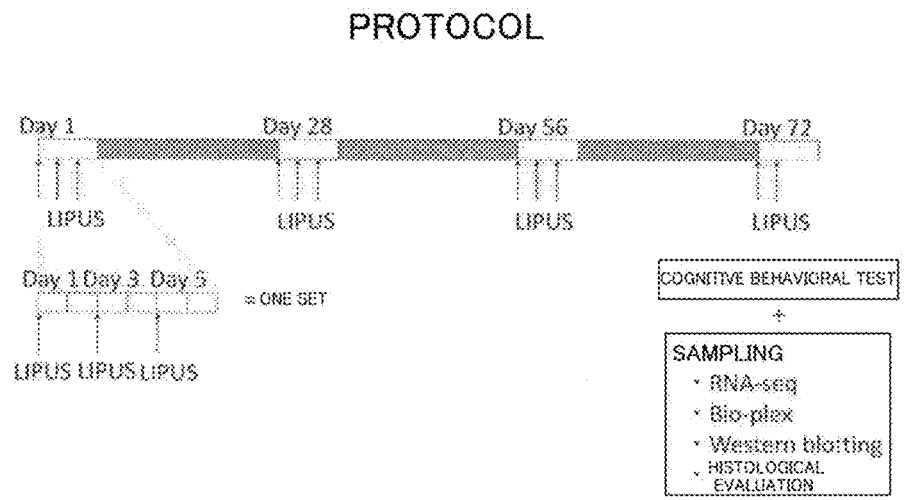
FIG. 16 is a schematic view of a test method of Example 1-2. •From 3 months old, once a month: 20 minutes×3 times/day. •Sacrificed after cognitive behavioral test at 6 months old. •Irradiation conditions are the same as in the BCAS model.

With the use of transgenic mice (SXFAD) serving as an Alzheimer's disease mouse model, ultrasound treatment was performed in the same manner as with the BCAS model in accordance with a protocol illustrated in FIG. 16. The SXFAD model was subjected to one set of ultrasound treatment once every month, and observed until 6 months old.

Figure 17:
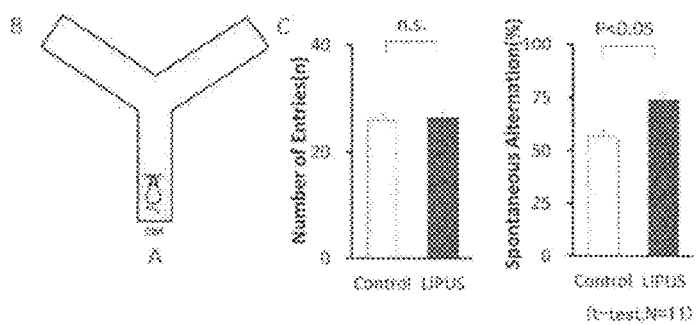
FIG. 17 are the outline of Example 1-2 and graphs for showing results thereof. Cognitive function evaluation: for suppression of cognitive dysfunction by LIPUS treatment. Results of a Y-maze test (method of evaluating cognitive function through utilization of the behavior of a mouse of choosing a path different from that the mouse has come down like A→B→C when having no/mal cognitive function).
Figure 18:
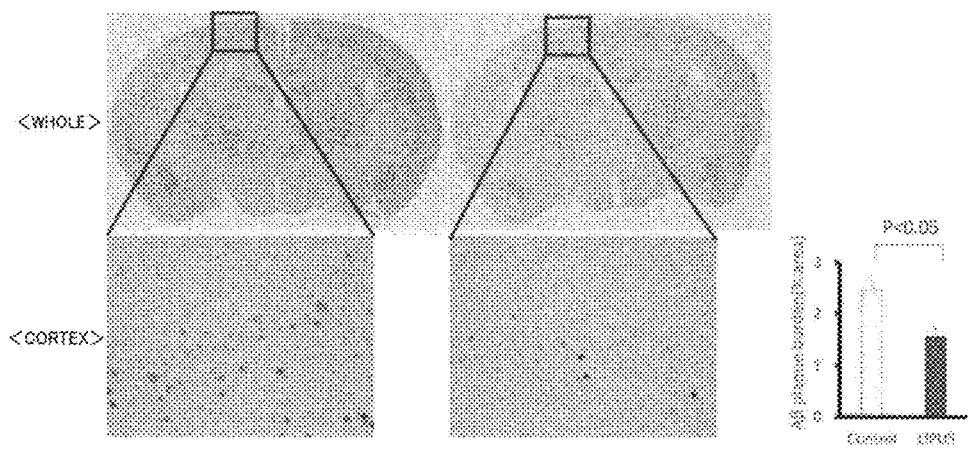
FIG. 18 are images and a graph for showing results of Example 1-2 (accumulation of amyloid-β in a tissue). LIPUS treatment may decrease the accumulation of amyloid-β.

The results are shown in FIG. 17 and FIG. 18. As shown in FIG. 17, the ultrasound treatment suppressed cognitive dysfunction. In FIG. 18, 4G8 immunostained images (amyloid-β staining) are shown. As shown in FIG. 18, the possibility that the accumulation of amyloid-β was reduced by the ultrasound treatment was suggested. Molecular expression analysis found significant expression of endothelial nitric oxide synthase (eNOS) resulting from the ultrasound treatment, suggesting the possibility that the eNOS contributed to the improvement of cognitive function.

Example 2 Investigation on Ultrasound Irradiation Method in Humans Taking Safety into Consideration The following are available as safety standards for ultrasound irradiation.
(1) 720 mW/cm$^2$ or less recommended by the global maximum acoustic output (AO)
(2) 500 mW/cm$^2$ or less recommended by Tyles's stated limit Therefore, in the following investigation, ultrasound irradiation was performed in the range of an ISPTA of 250 mW/cm$^2$ or less.

Factors capable of clinically influencing the intensity of ultrasound for treatment were verified using human skulls. The temporal bones of a total of seven 67- to 96-year-old, male and female donated bodies were collected, were each measured for its bone density and bone thickness, and were then each measured for its ultrasound transmittance.

Figure 19:
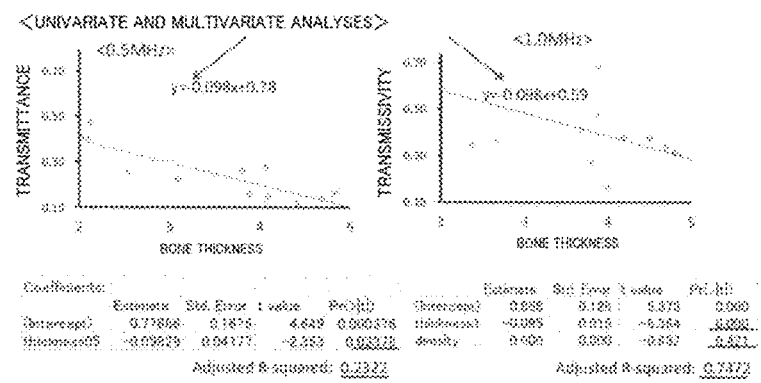
FIG. 19 is a schematic explanatory diagram of a case in which irradiation is performed at an interval of 0.3 ms between the start of ultrasound irradiation from one probe and the start of ultrasound irradiation from another probe in Example 2 (Investigation using a human skull. Relationship between bone density/bone thickness and ultrasound transmittance). Slopes at 0.5 MHz and 1.0 MHz coincidentally coincided. It is thought that only the thickness needs to be considered. Therefore, the transmittance can be predicted from the thickness.

The test was performed at 0.5 MHz and 1.0 MHz. The results were as described below. At 0.5 MHz, a correlation coefficient between transmissivity and the bone thickness was −0.53, and a correlation coefficient between the bone density and the transmissivity was 0.30. At 1.0 MHz, a correlation coefficient between the transmissivity and the bone thickness was −0.88, and a correlation coefficient between the transmissivity and the bone density was −0.30. On the basis of those data, for example, multivariate analysis was performed for 1.0 MHz, and as a result, it was found that the transmissivity and the bone thickness had a significance of P<0.001, but there was no significant tendency between the transmissivity and the bone density. The results suggested that only the "bone thickness" needed to be considered as a parameter on the patient side. In this case, Adjusted R-squared (coefficient of determination adjusted for degree of freedom) was 0.7472, suggesting that it was possible to predict the transmissivity from the bone thickness. Regression analysis found a correlation between the bone thickness and the ultrasound transmittance. In FIG. 19, results obtained by further performing multivariate analysis are shown. There was no correlation between the bone density and the ultrasound transmittance, a significant correlation was found between the bone thickness and the ultrasound transmittance, and the R-squared was high for the results at 1.0 MHz, showing that it was possible to predict the transmittance from the value of the thickness. That is, it was shown that only the bone thickness served as a factor needed as a parameter on the patient side in transcranial ultrasound irradiation.

Figure 20:
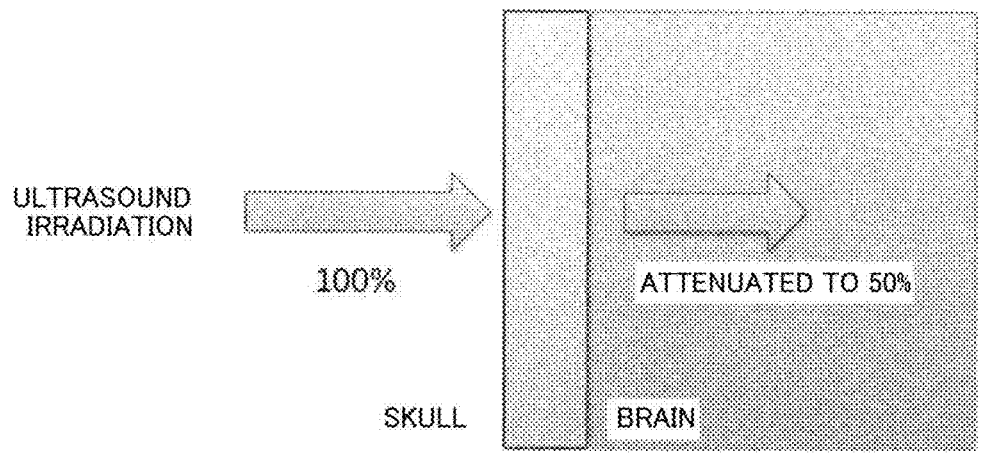
FIG. 20 is an illustration of test results for the relationship between the bone density or bone thickness and the ultrasound transmittance in Example 2.

Further, at a general thickness of a human temporal bone of from about 2 mm to about 3 mm, in the case of, for example, a frequency of 0.5 MHz, an ultrasound transmittance for one time of bone-brain transmission is from 25% to 50% in terms of power (from 50% to 70% in terms of amplitude) (FIG. 20). Therefore, ultrasound radiated from an ultrasound probe has already been attenuated by 25% to 50% in terms of power at the time of reaching the brain.

Figure 21:
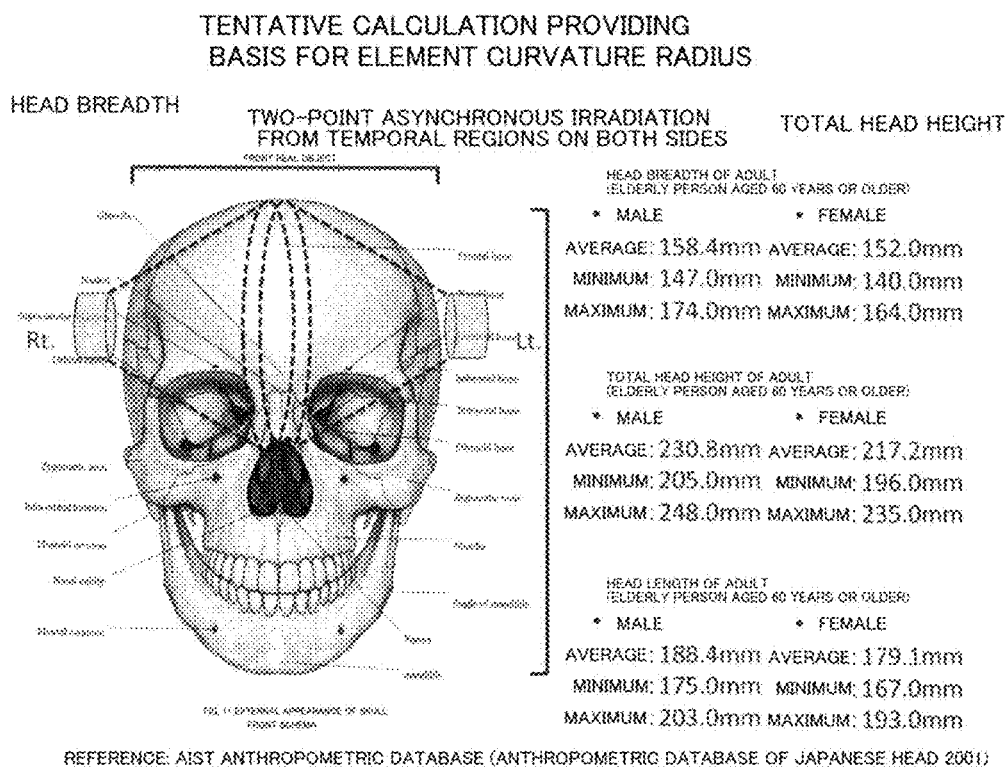
FIG. 21 is an explanatory diagram regarding an investigation on an irradiation angle for propagating ultrasound to a wide range of the brain in Example 2.

In the case of two-point alternate irradiation from probes at right and left temporal regions (FIG. 21), when the propagation speed of ultrasound in the brain is assumed to be 1,540 m/s, a wavelength at 500 kHz is 3.08 mm, and 32 waves travel 3.08×32=98.56 mm in one pulse. In FIG. 21, averages values for the head breadth, total head height, and head length of adults, and the like described in the AIST anthropometric database (Anthropometric Database of Japanese Head 2001) (https://www.dh.aist.go.jp/database/head/#stats) are shown. From the above-mentioned values, when the shortest diameter of the head is assumed to be 174 mm (database, maximum diameter of male head breadth), the period of time required for reaching the contralateral skull is 0.174 m/1,540 m/s=0.113 ms.

Meanwhile, ultrasound absorption in the brain becomes stronger at a higher frequency (about 1 dB/cm/MHz). The power becomes 1/100 in the case of 20 dB attenuation, and hence under the condition of 0.2 dB/cm at 0.5 MHz (see the table on p. 731 of Ultrasound Handbook, Maruzen Publishing Co., Ltd., published in 1999), 100 cm propagation is required for the power to become 1/100. That is, it is considered that, when irradiation is performed at an interval of 1 m/1,540 m/s=0.00065 s=0.65 ms, the influence of a previously radiated wave is negligible.

In actuality, in 100 cm propagation, reflection by bone occurs 100 cm/17.4 cm=6 times, and hence further safety is achieved by virtue of the influence of the reflection (exit through the bone).

According to the investigation using the human skull described above, the attenuation of ultrasound in one time of bone-brain transmission is from about a half to about 70% in terms of amplitude, and in this case, corresponds to from 25% to 50% in terms of power. This suggests that irradiation at an interval of 0.3 ms does not cause a problem (the power is halved by passing through bone, and the power becomes 1/50 through attenuation in the brain).

Figure 22:
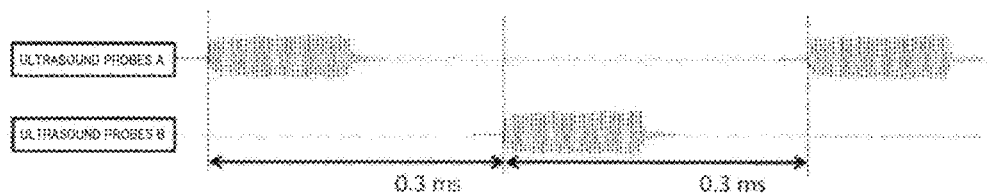
FIG. 22 is a graph for showing test results for the relationship between the bone density or bone thickness and the ultrasound transmittance in Example 2.

Therefore, when irradiation is performed at an interval of 0.3 ms between the start of ultrasound irradiation from one probe and the start of ultrasound irradiation from another probe (FIG. 22), the duty ratio is 10 cm/50 cm=20% at 0.5 MHz. In view of the foregoing, it is considered that there is no possibility of a local energy increase due to an interference wave at 0.5 MHz and a duty ratio of less than 20%.

Figure 23:
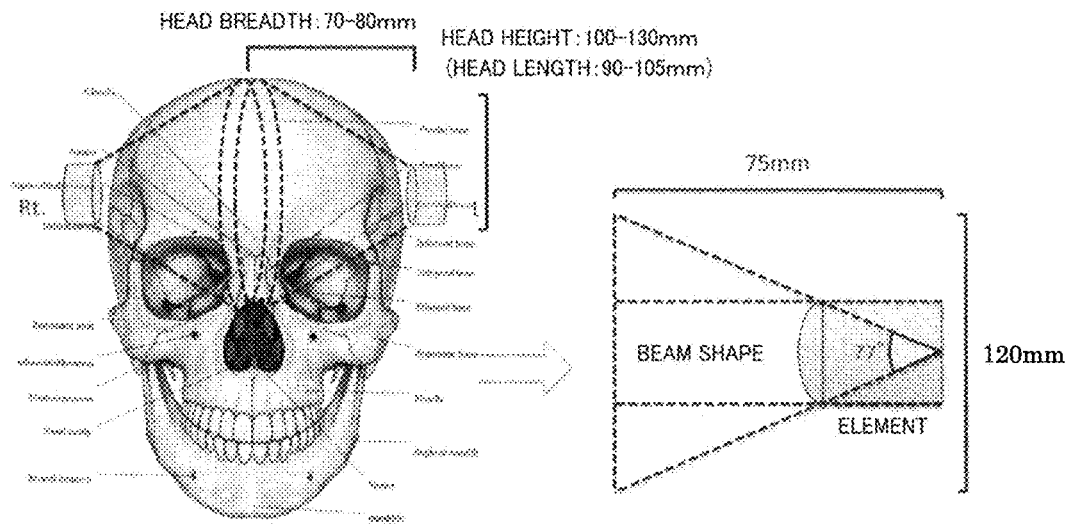
FIG. 23 is an explanatory diagram regarding an investigation on an irradiation angle for propagating ultrasound to a wide range of the brain in Example 2 (Calculation providing the basis for an element curvature radius. Ideal irradiation range estimated from the head height, head breadth, and head length of a human skull. In this case, it was considered that a lens needed a convexity of 15 mm. A required irradiation angle of from 60° to 90° is assumed.

In addition, it is considered that ultrasound can be propagated to the entire brain by radiating, from a temple, such ultrasound that the spreading angle of the inclined surface of unfocused ultrasound energy in an inversely tapered shape enlarging in diameter is 77° using a cylindrical probe in which the diameter of a portion from which ultrasound is radiated is set to 33 mm on the assumption that the head breadth and head height of a subject are from 70 mm to 80 mm and from 100 mm to 130 mm, respectively (FIG. 23).

It is considered that, when ultrasound irradiation is performed under the above-mentioned conditions, a dementia treatment effect is obtained also in humans by physical stimulation with ultrasound in the same manner as in Example 1 described above.

Example 3 Test Demonstrating Efficacy of Instrument

In order to reveal the effectiveness of this instrument for two major pathological conditions of dementia, i.e., cerebrovascular dementia (Vascular Dementia; VaD) and dementia of the Alzheimer's type (Alzheimer's Disease; AD), investigations were performed using respective mouse models. Results showing major effectiveness in this instrument are described below. Of those results, the results of a cognitive function test considered to serve as an end point in clinical settings as well, and cerebral blood flow considered to be the most important factor in a mechanism investigation thereon are shown with graphs.

3-1 Investigation Using VaD Model Mice

Figure 24:
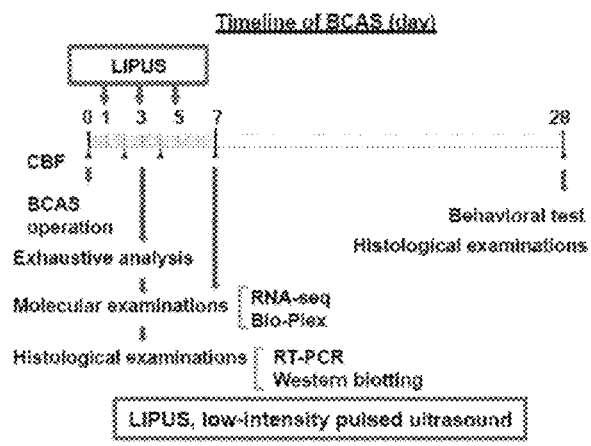
FIG. 24 is an illustration of a treatment schedule in Example 3-1.

Bilateral common carotid artery stenosis (BCAS) mice were generated as a VaD model, and divided into a LIPUS group (treated group) or a control group (non-treated group). With LIPUS set to be radiated to the entire brain from the day after BCAS operation, a therapeutic intervention was performed according to a schedule illustrated in FIG. 24. After LIPUS treatment, follow-up observation was performed until 28 days after operation, and the measurement of cerebral blood flow and a cognitive behavioral test were performed. In addition, a whole-brain tissue was used to perform biochemical analysis based on exhaustive analysis by RNA-sequencing and Bio-plex, and evaluation by tissue immunostaining.

3-1-1 Analysis of Temporal Change in Cerebral Blood Flow Using VaD Model Mice

Figure 25:
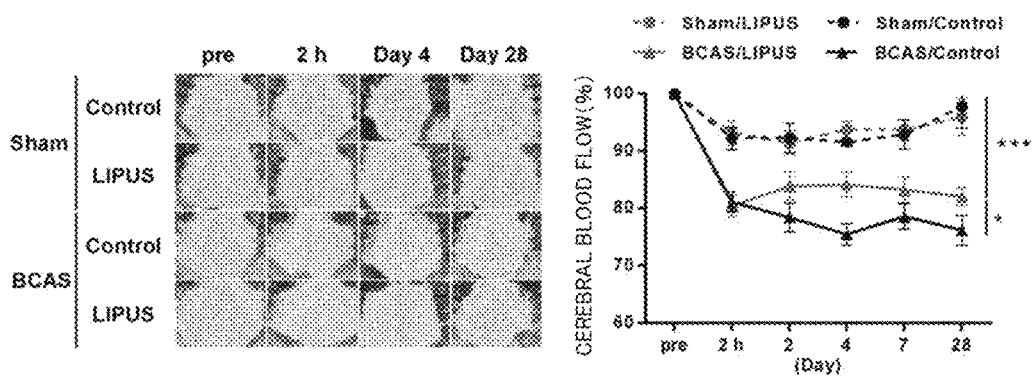
FIG. 25 are images and a graph for showing results of Example 3-1-1.

After the therapeutic intervention, cerebral blood flow was measured at 2 hours, 4 days, and 28 days thereafter, and as a result, it was found that a decrease in cerebral blood flow was significantly suppressed in the LIPUS group (FIG. 25) (n=9-10, sham; n=20-25, BCAS) (*P<0.05; ***P<0.0005; two-way ANOVA, multiple t-test). All results are expressed as mean±standard error.

3-1-2 Cognitive Function Test Using VaD Model Mice

Figure 26:
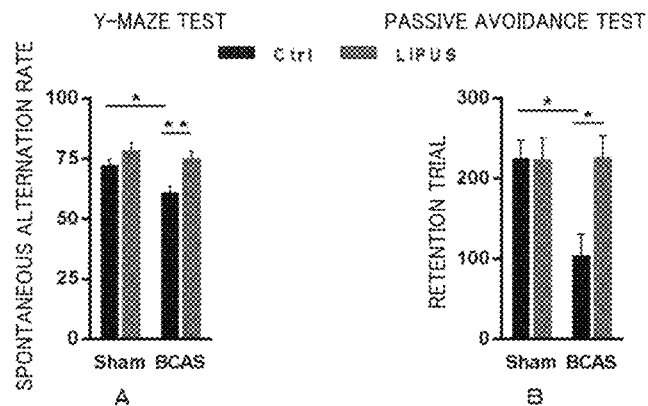
FIG. 26 are graphs for showing results of Example 3-1-2.

A Y-maze test and a passive avoidance test were performed 28 days after the therapeutic intervention, and as a result, it was found that cognitive dysfunction was significantly suppressed in the LIPUS group (FIG. 26A and FIG. 26B) (sham; n=12-16, BCAS; n=13-17) (*P<0.05, **P<0.005; two-way ANOVA, multiple t-test). All results are expressed as mean±standard error. In addition, this effect was maintained until 3 months after operation (P<0.05).

3-1-3 Biochemical Analysis of Influence by Ultrasound Treatment Using VaD Model Mice The ultrasound treatment was found to significantly enhance the expressions of genes associated with angiogenesis/oligodendrocyte precursor cells (Olig2; P<0.05, eNOS; P<0.05, CXCR4; P<0.05, FGF2; P<0.05). In addition, analysis by Western blotting found significant enhancement of expressions mainly of angiogenesis molecules (eNOS; P<0.05, CXCR4; P<0.05, FGF2; P<0.005, VEGF; P<0.05), and also found significant enhancement of the expressions of neurotrophic factors (BDNF; P<0.05, NGF; P<0.05). Here, Olig2 represents oligodendrocyte transcription factor 2, eNOS represents endothelial nitric oxide synthase, CXCR4 represents CXC chemokine receptor 4, FGF2 represents fibroblast growth factor 2, VEGF represents vascular endothelial growth factor, BDNF represents brain-derived neurotrophic factor, and NGF represents nerve growth factor.

3-1-4 Histological Analysis of Influence of Ultrasound Treatment Using VaD Model Mice The ultrasound treatment reduced white matter injury (P<0.05), and promoted the growth of angiogenesis/oligodendrocyte precursor cells (P<0.05 for each). In addition, immature nerve cells were increased (P<0.05).

3-2 Investigation Using AD Model Mice

Figure 27:
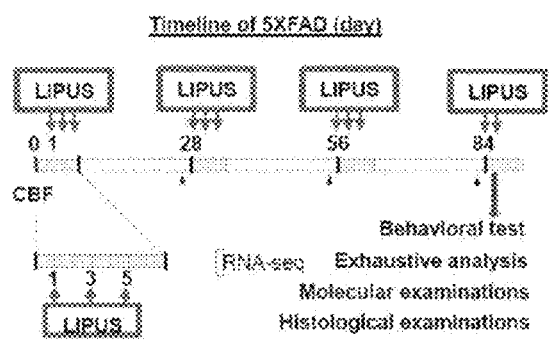
FIG. 27 is an illustration of a treatment schedule in Example 3-2.

Effectiveness and safety for AD were confirmed using 5×FAD transgenic mice as an AD model. An evaluation method was performed in conformity with the VaD model. The 5×FAD transgenic mice were divided into a LIPUS group (treated group) or a control group (non-treated group). With LIPUS set to be radiated to the entire brain, a therapeutic intervention was performed according to a schedule illustrated in FIG. 27. After LIPUS treatment, follow-up observation was performed until 28 days after operation, and the measurement of cerebral blood flow and a cognitive behavioral test were performed. In addition, a whole-brain tissue was used to perform biochemical analysis based on exhaustive analysis by RNA-sequencing and Bio-plex, and evaluation by tissue immunostaining.

3-2-1 Analysis of Temporal Change in Cerebral Blood Flow Using AD Model Mice

Figure 28:
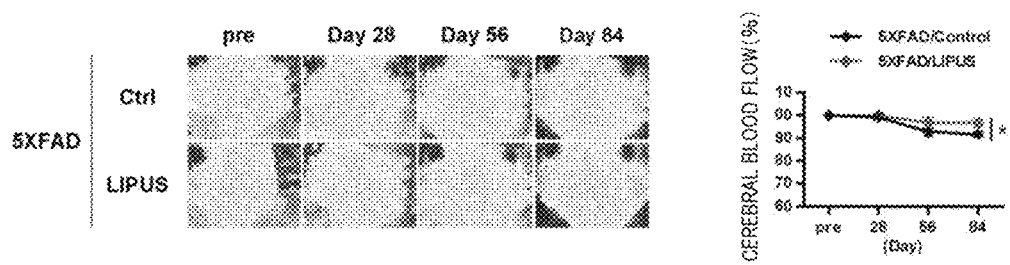
FIG. 28 are images and a graph for showing results of Example 3-2-1.

At 3 months from the initial treatment, the blood flow through the entire brain was significantly retained in the LIPUS group (FIG. 28) (n=14 in each group) (*P<0.05, t-test). All results are expressed as mean±standard error.

3-2-2 Cognitive Function Test Using AD Model Mice

Figure 29:
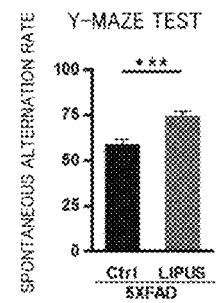
FIG. 29 is a graph for showing results of Example 3-2-2.

After the therapeutic intervention, a Y-maze test was performed, and as a result, it was found that cognitive dysfunction was significantly suppressed in the LIPUS group 3 months after the initial treatment (FIG. 29) (n=18 in each group) (***P<0.0005, t-test). All results are expressed as mean±standard error.

3-2-3 Biochemical Analysis of Influence of Ultrasound Treatment Using AD Model Mice (Neurotrophic Factors)

In the LIPUS group, the expressions of eNOS and neurotrophic factors were significantly enhanced (eNOS; P<0.05, BDNF; P<0.05, NGF; P<0.05), and besides, amyloid-$\beta$ (42) was decreased (P<0.05).

3-2-4 Biochemical Analysis of Influence of Ultrasound Treatment Using AD Model Mice (Amyloid-$\beta$)

The ultrasound treatment significantly reduced the accumulation of amyloid-$\beta$ (42) in the entire brain (P<0.05). In addition, microgliosis was significantly reduced (P<0.05) and angiogenesis was found to tend to be promoted (P=0.19).

Figure 30:
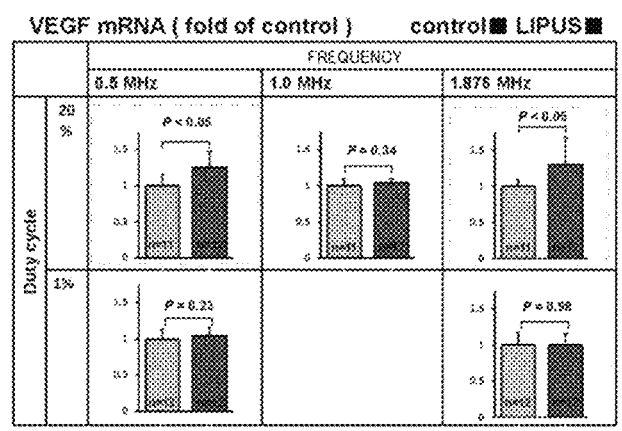
FIG. 30 are graphs for showing results of Example 4-1.

Example 4 Test Demonstrating Use Method for Instrument 4-1 Investigation on Optimal Frequency Condition In the evaluation of ultrasound transmissivity using a human temporal bone (site at which the treatment instrument was to be externally fitted), the transmittance had a higher value at a lower frequency (y=−0.098x+0.59, predicted transmittance for 2 cm of skull: 60.6%; 0.5 MHz, y=−0.098x+0.78, predicted transmittance for 2 cm of skull: 41.6%; 1.0 MHz) (FIG. 19). In addition, relationships of the frequency with a mechanical index (MI) and a the/mal index (TI) have been described, though the report is about focused ultrasound. A frequency of the following condition was about 0.5 MHz: the condition was close to the condition of 99 mW/cm$^2$ in a basic investigation with mice in which effectiveness was found; and the condition was one under which cavitation did not occur in the brain (MI value 0.25; one-fourth of MI value=1.0, a condition for cavitation occurrence in water as a worse case) and was one under which an excessive temperature increase did not occur (TI did not increase by 2° C. or more). Further, in an in vitro experiment using human umbilical vein endothelial cells, the enhancement of the expression of VEGF was found even at a frequency of 0.5 MHz (P<0.05) (FIG. 30). In view of the foregoing, in consideration of transmissivity and safety, 0.5 MHz is considered to be optimum.

4-2 Investigation on Optimal Duty Ratio

Figure 31:
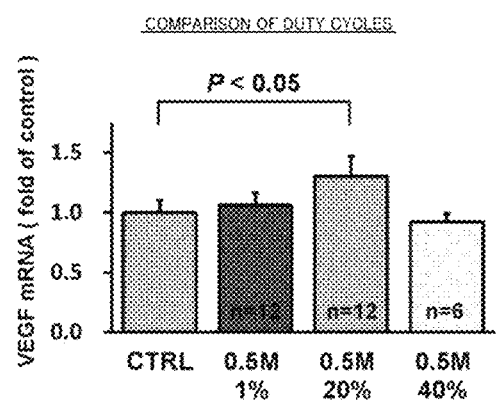
FIG. 31 is a graph for showing results of Example 4-2.

In the in vitro experiment using human umbilical vein endothelial cells, a change in VEGF expression was evaluated by changing the duty ratio condition among 1%, 20%, and 40% while fixing the frequency at 0.5 MHz. The results were as follows: no enhancement of the expression of VEGF was found at duty ratios of 1% and 40%, but a significant enhancement of the expression of VEGF was found at a duty ratio of 20% (P<0.05) (FIG. 31). In view of the foregoing, a duty ratio of about 20% is considered to be optimum at a frequency of 0.5 MHz, but 20% or less is desirable in light of the tentative calculation for safety regarding an interference wave, and hence it is considered that the optimal duty ratio is 20% (10% from each probe).

4-3 Investigation on Optimal Treatment Conditions

Irradiation conditions for treatment were investigated using cultured vascular endothelial cells. In the range of from 0.05 MPa to 2.2 MPa serving as an acoustic pressure settable in a convex transducer, the cultured vascular endothelial cells were subjected to ultrasound irradiation, and the mRNA expressions of VEGF, FGF2, and eNOS were evaluated. The effectiveness of this treatment is considered to correlate with the expression amounts of VEGF, FGF2, and eNOS. Therefore, in this investigation, irradiation conditions were judged to be effective when the mRNA expression amounts thereof had significantly high values as compared to those in the control group.

Figure 32:
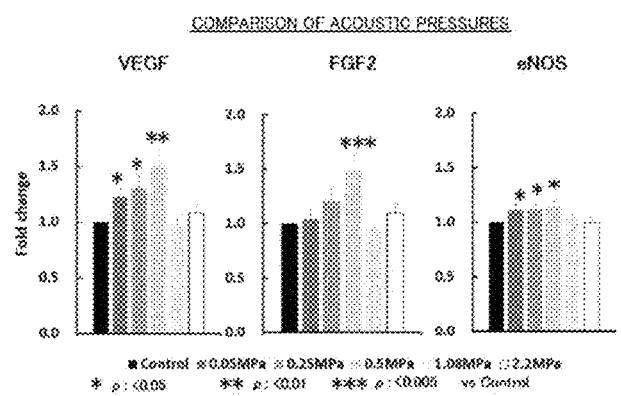
FIG. 32 are graphs for showing results of Example 4-3.
Figure 33:
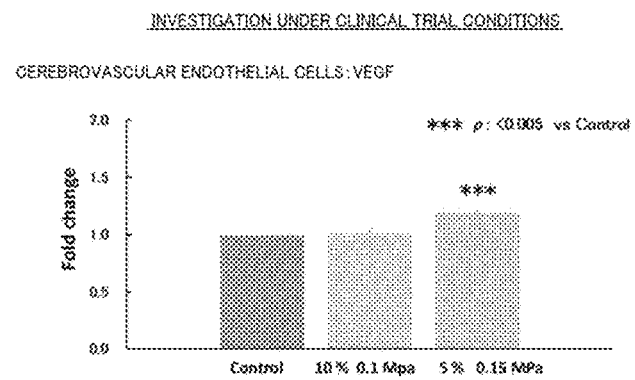
FIG. 33 is a graph for showing results of Example 4-3.

As the results are shown in FIG. 32, it was shown that it was important to set the tissue amplitude to from 0.05 MPa to 0.5 MPa. In order to achieve this acoustic pressure in a brain tissue, it was estimated that an acoustic pressure directly under an element desirably fell within the range of from 0.1 MPa to 1.5 MPa.

Next, in consideration of an increase in contact temperature at a patient contact portion as well, the expression amount of VEGF was evaluated using cerebrovascular endothelial cells under the following two sets of conditions: conditions 1: acoustic pressure directly under element: 1.3 MPa (tissue amplitude: 0.15 MPa) and total duty ratio: 5%; and conditions 2: acoustic pressure directly under element: 0.9 MPa (tissue amplitude: 0.1 MPa) and total duty ratio: 10%. As a result, the expression amount of VEGF had a significantly high value under the conditions 1, and hence it was judged that the conditions 1 were desirable treatment conditions.

4-4 Optimal Settings of Treatment Time/Period

In a basic investigation using two different AD model mice, effectiveness was found under the treatment conditions of 20 minutes×3 times. In addition, with regard to a treatment period, follow-up observation until 3 months after treatment in the cerebrovascular dementia model found that the suppression of cognitive dysfunction found in the ultrasound-treated group was maintained until 3 months after operation (P<0.05). In view of the foregoing, it may be appropriate to perform treatment every 3 months under the conditions of 20 minutes×3 times.

INDUSTRIAL APPLICABILITY

As described above, the number of dementia patients is as many as about 2,600,000 in Japan alone, and besides, the number is continuously increasing. Accordingly, there is a strong need for the development of a novel treatment method therefor. Therefore, the present invention, which can provide a novel method of treating dementia different from related-art drug treatment or the like, is extremely useful.

The invention claimed is:

1. A device for treating dementia, comprising:
a plurality of ultrasound probes;
an ultrasound transducer arranged in each of the ultrasound probes and configured to propagate unfocused ultrasound energy to an entirety of a brain; and
an ultrasound generator connected to each of the ultrasound probes,
wherein the ultrasound generator is configured to control the ultrasound transducer so as to sequentially radiate the unfocused ultrasound energy between the plurality of ultrasound probes,
wherein a frequency of the radiated unfocused ultrasound energy is set within a range of from 0.5 megahertz ("MHz") to 0.8 MHz,
wherein the radiated unfocused ultrasound energy is a non-continuous wave, and a number of cycles thereof is set within a range of from 1 cycle to 64 cycles,
wherein the unfocused ultrasound energy irradiation from the plurality of ultrasound probes is performed at an interval of 0.30/f ms or more, where f represents a frequency (MHz) of a pulse to be transmitted,
wherein a sound pressure of radiated ultrasound directly under the ultrasound transducer is within a range of from 0.1 MegaPascal ("MPa") to 1.5 MPa,
wherein a treatment time with ultrasound is set within a range of 15 to 60 minutes,
wherein the dementia is treated by enhancing expression of endothelial nitric oxide synthase ("eNOS"),
wherein the unfocused ultrasound energy is diffused in an inversely tapered shape gradually enlarging in diameter toward a radiation direction,
wherein a spreading angle of an inclined surface of the unfocused ultrasound energy in the inversely tapered shape enlarging in diameter is from 50° to 100°, and
the ultrasound generator is configured to stimulate vascular endothelial cells by applying an average intensity of 720 mW/cm$^2$ or less to enhance the expression of eNOS, VEGF, and bFGF.

2. The device according to claim 1, wherein the plurality of ultrasound probes each further include an ultrasound receiving element for receiving ultrasound radiated from mutually different ultrasound probes and transmitted through the brain.

3. The device according to claim 2, further comprising means for evaluating a treatment effect of ultrasound in accordance with a received intensity of the transmitted ultrasound.

4. The device according to claim 2, further comprising output adjusting means for adjusting an output of ultrasound to be output in accordance with a received intensity of the transmitted ultrasound.

5. A program stored in a device for treating dementia, the device including:
- a plurality of ultrasound probes;
- an ultrasound transducer arranged in each of the ultrasound probes and configured to propagate unfocused ultrasound energy to an entirety of a brain; and
- an ultrasound generator connected to each of the ultrasound probes,
- the program being configured to cause the device to execute a function of causing the ultrasound transducer arranged in each of the ultrasound probes to generate unfocused ultrasound energy through control by the ultrasound generator,
- wherein the ultrasound generator is configured to control the ultrasound transducer so as to sequentially radiate the unfocused ultrasound energy between the plurality of ultrasound probes,
- wherein a frequency of the radiated unfocused ultrasound energy is set within a range of from 0.5 MHz to 0.8 MHz,
- wherein the radiated unfocused ultrasound energy is a non-continuous wave, and a number of cycles thereof is set within a range of from 1 cycle to 64 cycles,
- wherein the unfocused ultrasound energy irradiation from the plurality of ultrasound probes is performed at an interval of 0.30/f ms or more, where f represents a frequency (MHz) of a pulse to be transmitted,
- wherein a sound pressure of radiated ultrasound directly under the ultrasound transducer is within a range of from 0.1 MPa to 1.5 MPa,
- wherein a treatment time with ultrasound is set within a range of 15 to 60 minutes,
- wherein the dementia is treated by enhancing expression of endothelial nitric oxide synthase ("eNOS"),
- wherein the unfocused ultrasound energy is diffused in an inversely tapered shape gradually enlarging in diameter toward a radiation direction, and
- wherein a spreading angle of an inclined surface of the unfocused ultrasound energy in the inversely tapered shape enlarging in diameter is from 50° to 100°, and
- improving cognitive function by stimulating vascular endothelial cells by applying an average intensity of 720 mW/cm$^2$ or less to enhance the expression of eNOS, VEGF, and bFGF.

6. The device according to claim 1, wherein the radiated ultrasound is a non-continuous wave, and the number of cycles thereof is set in 32 cycles.

7. The program according to claim 5, wherein the treatment time is from 1 minute to 60 minutes per treatment and the treatment is performed 1 to 7 times in 5 to 10 days, and those treatments continue once in 1 to 4 months.

8. The device according to claim 1, for improving cognitive function by stimulating vascular endothelial cells to enhance the expression of eNOS, VEGF, and bFGF.

9. The device according to claim 1, wherein the dementia is Alzheimer's disease or vascular dementia.

10. The program according to claim 5, wherein the dementia is Alzheimer's disease or vascular dementia.

11. The device according to claim 1, for reducing at least one member selected from the group consisting of Amyloid β40 and Amyloid β42, wherein the dementia is Alzheimer's disease.

12. The program according to claim 5, for reducing at least one member selected from the group consisting of Amyloid β40 and Amyloid β42, wherein the dementia is Alzheimer's disease.

13. The device according to claim 1, wherein the dementia is cerebrovascular dementia.

* * * * *